(12) United States Patent
Locke et al.

(10) Patent No.: US 11,883,578 B2
(45) Date of Patent: Jan. 30, 2024

(54) LOW PROFILE DISTRIBUTION COMPONENTS FOR WOUND THERAPY

(71) Applicant: KCI Licensing, Inc., San Antonio, TX (US)

(72) Inventors: Christopher Brian Locke, Bournemouth (GB); Thomas Edwards, Southampton (GB)

(73) Assignee: 3M Innovative Properties Company, St. Paul, MN (US)

( * ) Notice: Subject to any disclaimer, the term of this patent is extended or adjusted under 35 U.S.C. 154(b) by 621 days.

(21) Appl. No.: 16/168,426

(22) Filed: Oct. 23, 2018

(65) Prior Publication Data

US 2019/0117861 A1   Apr. 25, 2019

Related U.S. Application Data

(60) Provisional application No. 62/678,585, filed on May 31, 2018, provisional application No. 62/575,974, filed on Oct. 23, 2017.

(51) Int. Cl.
*A61F 13/00* (2006.01)
*A61M 1/00* (2006.01)
*A61F 13/02* (2006.01)

(52) U.S. Cl.
CPC .......... *A61M 1/73* (2021.05); *A61F 13/00068* (2013.01); *A61F 13/0216* (2013.01);
(Continued)

(58) Field of Classification Search
CPC ............ A61M 1/90; A61M 1/73; A61M 1/85; A61M 1/74; A61M 2205/3344;
(Continued)

(56) References Cited

U.S. PATENT DOCUMENTS 1,355,846 A   10/1920   Rannells
2,547,758 A   4/1951    Keeling
(Continued)

FOREIGN PATENT DOCUMENTS

AU   550575 B2   3/1986
AU   745271 B2   3/2002
(Continued)

OTHER PUBLICATIONS

"Teflon Properties", W.S. Hampshire, Inc., http://catalog.wshampshire.com/asset/psg_teflon_ptfe.pdf. Accessed 2021 (Year: 2021).*

(Continued)

*Primary Examiner* — Kai H Weng

(57) ABSTRACT

Systems, apparatuses, and methods for providing negative pressure to a tissue site are disclosed. Illustrative embodiments may include an apparatus or system for delivering negative-pressure to a tissue site, which can be used in conjunction with low-profile distribution components for wound therapy. Such apparatus may include a low-profile dressing interface or connector comprising at least two side-by-side fluid pathways fluidly coupled to a recessed space of the connector, one for providing negative pressure to a tissue interface or manifold and the other for sensing the negative pressure within the recessed space adjacent the tissue interface. In some embodiments, for example, the apparatus may comprise a first layer of polymeric film having an outer surface, an inner surface, and a plurality of features extending from the inner surface, and a second layer of polymeric film coupled to the first layer. The second layer may have an outer, tissue-facing surface and an inner surface coupled to the first layer and covering the plurality of features to form an enclosed space with the inner surface of the first layer and a plurality of flow channels within the enclosed space. The second layer also includes an aperture
(Continued)

defining the recessed space adapted to fluidly coupling the enclosed space to the tissue interface.

23 Claims, 26 Drawing Sheets

(52) U.S. Cl.
CPC .............. *A61M 1/90* (2021.05); *A61M 1/913* (2021.05); *A61M 1/915* (2021.05); *A61M 1/92* (2021.05); *A61M 1/966* (2021.05); *A61F 13/0223* (2013.01); *A61F 2013/00536* (2013.01); *A61M 1/74* (2021.05); *A61M 2205/3344* (2013.01)

(58) Field of Classification Search
CPC ............ A61F 13/00068; A61F 13/0216; A61F 13/0223; A61F 2013/00536
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Toyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A * | 8/1995 | Todd ....................... | A61M 1/90 604/313 |
| 5,458,141 A | 10/1995 | Neil | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| D663,431 S | 7/2012 | Parker, III et al. | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| D686,329 S | 7/2013 | Traboulsi et al. | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| D707,830 S | 6/2014 | Klutts | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| D744,659 S | 12/2015 | Bishay et al. | |
| 9,198,801 B2 | 12/2015 | Weston | |
| 9,211,365 B2 | 12/2015 | Weston | |
| 9,289,542 B2 | 3/2016 | Blott et al. | |
| 9,693,907 B2 | 7/2017 | Locke et al. | |
| D806,256 S | 12/2017 | Allen et al. | |
| 10,537,478 B2 | 1/2020 | Holm et al. | |
| D885,587 S | 5/2020 | Park | |
| D887,563 S | 6/2020 | Caneppele et al. | |
| D890,936 S | 7/2020 | Hicken et al. | |
| 10,702,419 B2 | 7/2020 | Locke et al. | |
| D893,034 S | 8/2020 | Kase et al. | |
| D898,925 S | 10/2020 | Kelbie et al. | |
| 2002/0077661 A1 | 6/2002 | Saadat | |

(56) References Cited

U.S. PATENT DOCUMENTS

| | | | |
|---|---|---|---|
| 2002/0115951 A1 | 8/2002 | Norstrem et al. | |
| 2002/0120185 A1 | 8/2002 | Johnson | |
| 2002/0143286 A1 | 10/2002 | Tumey | |
| 2008/0195017 A1 | 8/2008 | Robinson et al. | |
| 2010/0160877 A1* | 6/2010 | Kagan | A61M 1/90 604/319 |
| 2012/0143113 A1* | 6/2012 | Robinson | A61F 13/00042 604/319 |
| 2012/0308780 A1 | 12/2012 | Rottger et al. | |
| 2013/0296816 A1 | 11/2013 | Greener | |
| 2014/0039424 A1 | 2/2014 | Locke | |
| 2014/0163491 A1 | 6/2014 | Schuessler et al. | |
| 2015/0080788 A1 | 3/2015 | Blott et al. | |
| 2015/0141941 A1* | 5/2015 | Allen | A61F 13/00068 604/319 |
| 2015/0245950 A1 | 9/2015 | Locke et al. | |
| 2015/0320603 A1 | 11/2015 | Locke et al. | |
| 2016/0059009 A1* | 3/2016 | Skiba | A61N 1/325 604/23 |
| 2016/0120706 A1 | 5/2016 | Collinson et al. | |
| 2017/0143552 A1* | 5/2017 | Hartwell | A61F 13/0233 |
| 2017/0189236 A1 | 7/2017 | Locke et al. | |
| 2017/0312402 A1 | 11/2017 | McDonald | |
| 2018/0228654 A1 | 8/2018 | Sarangapani et al. | |
| 2019/0117861 A1 | 4/2019 | Locke et al. | |
| 2020/0146897 A1 | 5/2020 | Locke et al. | |
| 2020/0353137 A1 | 11/2020 | Long et al. | |
| 2020/0375805 A1 | 12/2020 | Robinson et al. | |
| 2021/0161725 A1 | 6/2021 | Edwards et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| JP | 2009273669 A | 11/2009 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2010/068502 A1 | 6/2010 |
| WO | 2013/175306 A2 | 11/2013 |
| WO | 2014/184674 A2 | 11/2014 |
| WO | 2016193873 A1 | 12/2016 |

OTHER PUBLICATIONS

Partial International Search Report for Corresponding Application No. PCT/US2018/057109, dated Feb. 1, 2019.

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al.; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by

(56) References Cited

OTHER PUBLICATIONS

V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
Japanese Notice of Rejection for Corresponding Application No. 2019-006180, dated Nov. 26, 2019.
U.S. Non-Final Rejection for Corresponding U.S. Appl. No. 29/667,667, dated Jun. 14, 2021.
U.S. Restriction Requirement for Corresponding U.S. Appl. No. 29/667,667, dated Apr. 27, 2021.
U.S. Non-Final Rejection Corresponding to U.S. Appl. No. 16/525,376, dated May 20, 2021.
PTFE vs. Teflon: What's the Difference? by Teflon Coat, Performance Engineered Components, https://www.industrialcoat.com/ptfe-vs-teflon-whats-difference/, Aug. 8, 2018 (Year: 2018).
Definition of "Integral", Merriam-Webster Dictionary, https://www.merriam-webster.com/dictionary/integral, Accessed Dec. 15, 2021 (Year: 2021).
U.S. Non-Final Rejection Corresponding to U.S. Appl. No. 16/525,376, dated Jan. 4, 2022.
Definition of "Hollow", Merriam-Webster, https://www.merriam-webster.com/dictionary/hollow (year: 2021).
Definition of "Stack", Cambridge English Dictionary, https://dictionary.cambridge.org/us/dictionary/english/stack (year: 2021).
U.S. Final Rejection Corresponding to U.S. Appl. No. 16/525,376, dated Sep. 14, 2021.
Japanese Notice of Rejection Corresponding to Application No. 2020522357, dated Aug. 16, 2022.

\* cited by examiner

LOW PROFILE DISTRIBUTION COMPONENTS FOR WOUND THERAPY

RELATED APPLICATIONS

This application claims the benefit, under 35 U.S.C. § 119(e), of the filing of U.S. Provisional Patent Application Ser. No. 62/678,585, entitled "LOW PROFILE DISTRIBUTION COMPONENTS FOR WOUND THERAPY," filed May 31, 2018; and U.S. Provisional Patent Application Ser. No. 62/575,974, entitled "LOW PROFILE DISTRIBUTION COMPONENTS FOR WOUND THERAPY," filed Oct. 23, 2017 each of which is incorporated herein by reference for all purposes.

TECHNICAL FIELD

The invention set forth in the appended claims relates generally to tissue treatment systems and more particularly, but without limitation, to apparatuses and methods for providing negative-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage," respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and instillation therapy are widely known, improvements to therapy systems, components, and processes may benefit healthcare providers and patients.

BRIEF SUMMARY

New and useful systems, apparatuses, and methods for treating a tissue site in a negative-pressure therapy environment are set forth in the appended claims. Illustrative embodiments are also provided to enable a person skilled in the art to make and use the claimed subject matter. Some embodiments are illustrative of an apparatus or system for delivering negative-pressure to a tissue site, which can be used in conjunction with low-profile distribution components for negative-pressure therapy.

An example apparatus may be a low-profile, breathable, open conduit system that incorporates pressure feedback. In some embodiments, the apparatus may include a welded or laminated conduit structure with at least two fluid pathways, which are preferably pneumatically isolated from each other and the ambient environment.

In some examples, the conduit system may be a dressing interface configured to couple a dressing to a negative-pressure source. The two fluid pathways may be fluidly coupled to a recessed space of the dressing interface. One of the fluid pathways can provide negative pressure to a tissue interface or manifold, and the other fluid pathway can provide a feedback path for sensing the negative pressure within the recessed space adjacent the tissue interface.

In some embodiments, fluid pathways may be vertically stacked in a dressing interface. For example, the dressing interface may have first and second outer layers that are a flexible polymer film. Polyurethane or polyethylene may be suitable films in some examples. An intermediate third layer may be disposed between the outer layers to create two longitudinal chambers that run the length of the conduit structure. The first chamber may be configured as a feedback path, and the second chamber may be configured as a negative-pressure delivery path, for example. The film layers may be welded (RF or ultrasonic, for example) or bonded together to create a seal at least along their length. The distal end of the dressing interface may also be welded or bonded to seal the distal ends of the fluid pathways. A flange may be formed at a distal end of the dressing interface in some examples. A hole may be made near a distal end of at least two layers of the dressing interface. The holes may be configured to face a tissue site, and can provide a means for pressure and fluid to be communicated to and from a tissue site.

The longitudinal chambers may be filled with materials configured to provide flexibility and compressibility, and which can manifold fluid and pressure while being resistant to collapse and blockage under external compression.

For example, a chamber configured as a feedback path may be filled with a material that is open to pressure and fluid flow in the form of air, and is preferably hydrophobic to discourage ingress of exudate. The material also preferably resists blocking when compressed. Materials suitable for a feedback path may be reticulated foams (3-5 millimeters), felted and compressed reticulated foam (2-4 millimeters), combinations of foam and fabric, and coated or treated (e.g., plasma-treated) foam of manifolding structures. Additionally or alternatively, a feedback path may have a low-profile three-dimensional polyester textile, such as Baltex M3730 (3 millimeter) or a vacuum-formed structure of raised areas or closed cells to assist with pressure manifolding. In some embodiments, the top film layer may be a vacuum-formed film with raised structures to assist with manifolding.

A chamber configured as a negative-pressure delivery path may be filled with materials that are open to pressure and fluid flow in the form of air and exudate of varying viscosity, and is also preferably hydrophobic to discourage collection and clotting of exudate. Anti-clotting agents may also be bound to the material to further reduce clotting and blocking. The material in a negative-pressure delivery path may advantageously be less hydrophobic than the material in a feedback path to preference exudate and other liquid into the negative-pressure delivery path rather than the feedback path. The material in the negative-pressure delivery path is also preferably resistant to blocking under compression. This material may also be less flexible than material in a feedback path and, thus, even more resistant to compression. Materials suitable for this may be reticulated foam (3-8 millimeters) with a higher stiffness modulus than material in a feedback path. Other suitable materials may include combinations of foam and fabrics, coated or treated foam of manifolding structures, a low-profile three-dimensional textile, and one or more films with vacuum-formed raised structures or closed cells.

Additionally or alternatively, some examples of the intermediate layer may also comprise vacuum-formed blisters, bubbles, or closed cells that face the outer layer and align with similar features on that layer.

The materials of the dressing interface may be white or otherwise colored so that blood or infectious material may readily observed. The materials may be coated or formulated to provide anti-microbial properties to reduce the risk of bacterial colonization with extended wear times.

A proximal end of the dressing interface may be formed into a pneumatic connector, which may be connected in-line to a suitable adapter or may be connected directly to another distribution component.

More generally, some embodiments of an apparatus for providing negative-pressure treatment may comprise a first layer of polymer film having a first aperture, a second layer of polymer film having a second aperture, and a third layer of polymer film. The first layer, the second layer, and the third layer may be sealed to form a first fluid path and a second fluid path in a stacked relationship, and the second layer may be disposed between the first fluid path and the second fluid path. The first fluid path and the second fluid path may be fluidly coupled through the second aperture, and the first aperture and the second aperture are disposed at a distal end of the first fluid path. A first manifold may be configured to support the first fluid path, and a second manifold may be configured to support the second fluid path. A port may be fluidly coupled to a proximal end of the first fluid path and the second fluid path. The port may be configured to fluidly couple the first fluid path to a source of negative pressure and the second fluid path to a pressure sensor. In some embodiments, at least one of the first manifold and the second manifold may comprise a polymer film having bubbles or blisters.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
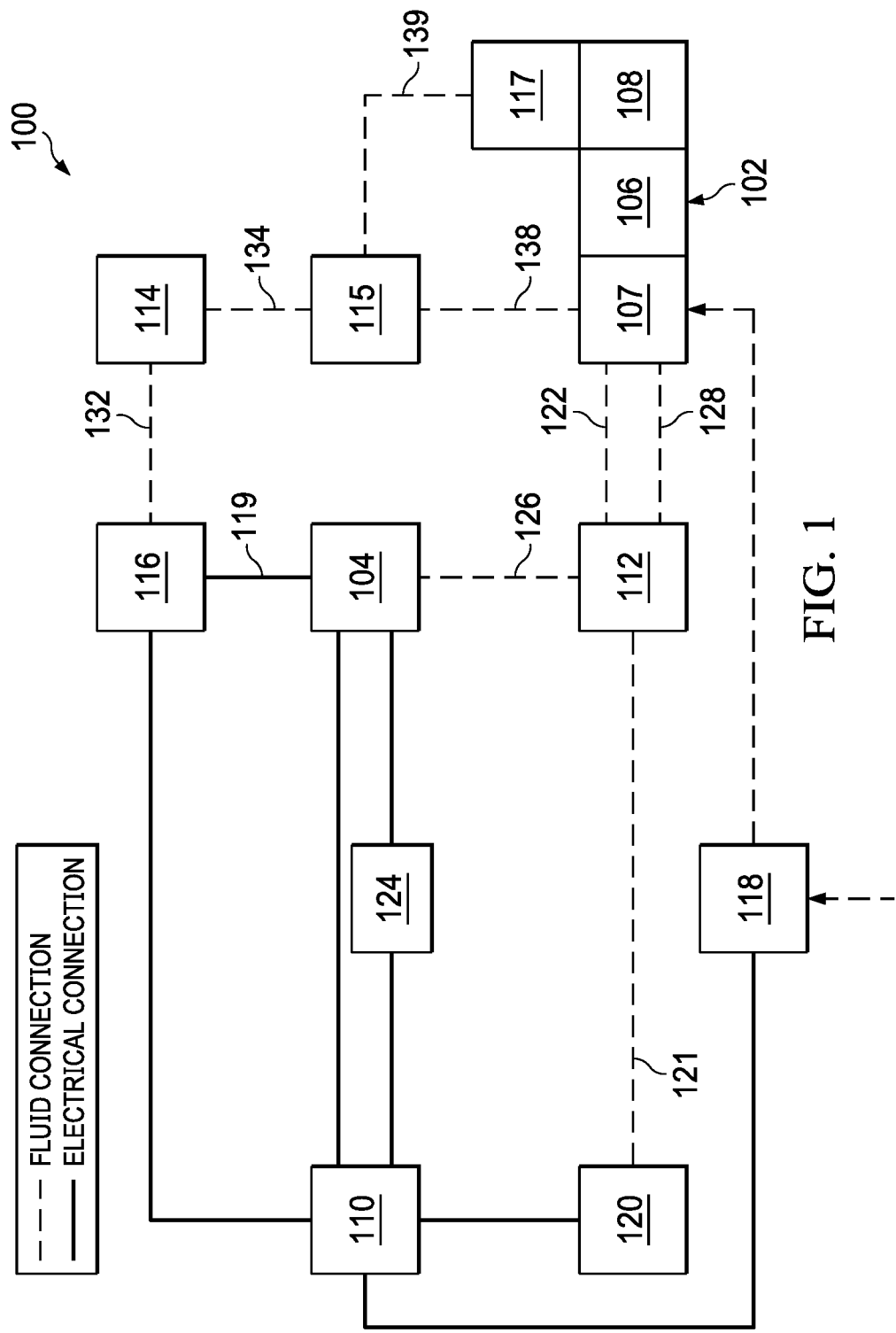
FIG. 1 is a functional block diagram of an example embodiment of a therapy system that can provide negative pressure and instillation in accordance with this specification.

FIG. 1 is a simplified functional block diagram of an example embodiment of a therapy system 100 that can provide negative-pressure therapy with instillation of treatment solutions in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds; partial-thickness burns; ulcers (such as diabetic, pressure, or venous insufficiency ulcers); flaps; and grafts, for example. The term "tissue site" may also refer to areas of any tissue that are not necessarily wounded or defective but are instead areas in which it may be desirable to add or promote the growth of additional tissue. For example, negative pressure may be applied to a tissue site to grow additional tissue that may be harvested and transplanted.

The therapy system 100 may include or be configured to be coupled to one or more distribution components. In general, a distribution component may refer to any complementary or ancillary component configured to be fluidly coupled to a negative-pressure supply between a negative-pressure supply and a tissue site. A distribution component is preferably detachable and may be disposable, reusable, or recyclable. For example, a dressing 102 is illustrative of a distribution component fluidly coupled to a negative-pressure source 104 in FIG. 1. A dressing may include a cover, a tissue interface, or both in some embodiments. The dressing 102, for example, may include a cover 106, a dressing interface 107, and a tissue interface 108. In some embodiments, the cover 106 may be configured to cover the tissue interface 108 and the tissue site, and may be adapted to seal the tissue interface and create a therapeutic environment proximate to a tissue site for maintaining a negative pressure at the tissue site. In some embodiments, the dressing interface 107 may be configured to fluidly couple the negative-pressure source 104 to the therapeutic environment of the dressing. The therapy system 100 may optionally include a fluid container, such as a container 112, coupled to the dressing 102 and to the negative-pressure source 104.

The therapy system 100 may also include a source of instillation solution, such as a solution source 114. A distribution component may be fluidly coupled to a fluid path between a solution source and a tissue site in some embodiments. For example, an instillation pump 116 may be coupled to the solution source 114, as illustrated in the example embodiment of FIG. 1. The instillation pump 116 may also be fluidly coupled to the negative-pressure source 104 such as, for example, by a fluid conductor 119. In some embodiments, the instillation pump 116 may be directly coupled to the negative-pressure source 104, as illustrated in FIG. 1, but may be indirectly coupled to the negative-pressure source 104 through other distribution components in some embodiments. For example, in some embodiments, the instillation pump 116 may be fluidly coupled to the negative-pressure source 104 through the dressing 102. In some embodiments, the instillation pump 116 and the negative-pressure source 104 may be fluidly coupled to two different locations on the tissue interface 108 by two different dressing interfaces. For example, the negative-pressure source 104 may be fluidly coupled to the dressing interface 107 at a first location, while the instillation pump 116 may be fluidly to the coupled to dressing interface 107 at a second location as shown in FIG. 1.

The therapy system 100 also may include sensors to measure operating parameters and provide feedback signals to the controller 110 indicative of the operating parameters. As illustrated in FIG. 1, for example, the therapy system 100 may include a first sensor 120 and/or a second sensor 124. The first sensor 120 may be configured to measure pressure in some examples. Other sensors, such as the second sensor 124, may be configured for measuring other properties in the therapy system 100 such as, for example, various pressures, voltages and currents. The first sensor 120 and the second sensor 124 may be electrically coupled to the controller 110 for providing information to the therapy system 100. The first sensor 120 may be fluidly coupled or configured to be fluidly coupled to a distribution component such as, for example, the negative-pressure source 104 either directly or indirectly through the container 112. The first sensor 120 may be configured to measure pressure in proximity to a tissue site, such as in the pressure in the dressing 102. In some example embodiments, the second sensor 124 may be in fluid communication with the output of the negative-pressure source 104 to directly measure the pump pressure (PP). In other example embodiments, the second sensor 124 may be electrically coupled to the negative-pressure source 104 to measure applied current as a proxy to the pump pressure.

Distribution components may be fluidly coupled to each other to provide a distribution system for transferring fluids (i.e., liquid and/or gas). For example, a distribution system may include various combinations of fluid conductors and fittings to facilitate fluid coupling. A fluid conductor generally includes any structure with one or more lumina adapted to convey a fluid between two ends, such as a tube, pipe, hose, or conduit. Typically, a fluid conductor is an elongated, cylindrical structure with some flexibility, but the geometry and rigidity may vary. Some fluid conductors may be molded into or otherwise integrally combined with other components. A fitting can be used to mechanically and fluidly couple components to each other. For example, a fitting may comprise a projection and an aperture. The projection may be configured to be inserted into a fluid conductor so that the aperture aligns with a lumen of the fluid conductor. A valve is a type of fitting that can be used to control fluid flow. For example, a check valve can be used to substantially prevent return flow. A port is another example of a fitting. A port may also have a projection, which may be threaded, flared, tapered, barbed, or otherwise configured to provide a fluid seal when coupled to a component.

In some embodiments, distribution components may also be coupled by virtue of physical proximity, being integral to a single structure, or being formed from the same piece of material. Coupling may also include mechanical, thermal, electrical, or chemical coupling (such as a chemical bond) in some contexts. For example, a tube may mechanically and fluidly couple the dressing 102 to the container 112 in some embodiments. In general, components of the therapy system 100 may be coupled directly or indirectly. For example, the negative-pressure source 104 may be directly coupled to the controller 110, and may be indirectly coupled to the dressing interface 107 through the container 112 by conduit 126 and conduit 128. The first sensor 120 may be fluidly coupled to the dressing 102 directly or indirectly by conduit 121 and conduit 122. Additionally, the instillation pump 116 may be coupled indirectly to the dressing interface 107 through the solution source 114 and the instillation regulator 115 by fluid conductors 132, 134 and 138. Alternatively, the instillation pump 116 may be coupled indirectly to the second dressing interface 117 through the solution source 114 and the instillation regulator 115 by fluid conductors 132, 134 and 139.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, coarse, or jagged profile that can induce strains and stresses on a tissue site, which can promote granulation at the tissue site.

In some embodiments, the tissue interface 108 may comprise or consist essentially of a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam manifold may vary according to needs of a prescribed therapy. For example, in some embodiments, the tissue interface 108 may be a foam manifold having pore sizes in a range of 400-600 microns. The tensile strength of the tissue interface 108 may also vary according to needs of a prescribed therapy. For example, the tensile strength of a foam may be increased for instillation of topical treatment solutions. In some embodiments, the tissue interface 108 may be reticulated polyurethane foam such as found in GRANUFOAM™ dressing or V.A.C. VERAFLO™ dressing, both available from Kinetic Concepts, Inc. of San Antonio, Texas.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WHITEFOAM™ dressing available from Kinetic Concepts, Inc. of San Antonio, Texas Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may comprise or consist essentially of, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 106 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 106 may comprise INSPIRE 2301 having an MVTR (upright cup technique) of 2600 g/m$^2$/24 hours and a thickness of about 30 microns.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives or combinations of adhesives may be applied in some embodiments to improve the seal and reduce leaks. Other example embodiments of an attachment device may include a double-sided tape, paste, hydrocolloid, hydrogel, silicone gel, or organogel.

In some embodiments, a dressing interface may facilitate coupling the negative-pressure source 104 to the dressing 102. The negative pressure provided by the negative-pressure source 104 may be delivered through the conduit 128 to a negative-pressure connector that, in some embodiments, may include an elbow connector (not shown) having a first end adapted to be positioned in fluid communication with the tissue interface 108 and a second end extending at a substantially right angle from the first end adapted to be fluidly coupled to the conduit 128. In some embodiments, the elbow connector may be substantially rigid. In yet another example embodiment, the negative-pressure interface may be semi-rigid such as, for example, a T.R.A.C.® Pad or Sensa T.R.A.C.® Pad available from KCI of San Antonio, Texas. The negative-pressure interface delivers negative pressure within an interior portion of the cover 106 and the tissue interface 108.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to control one or more operating parameters of the therapy system 100. Operating parameters may include, for example, the power applied to the negative-pressure source 104, the pressure generated by the negative-pressure source 104, or the pressure distributed to the tissue interface 108. The controller 110 is also preferably configured to receive one or more input signals and programmed to modify one or more operating parameters based on the input signals.

Sensors, such as the first sensor 120 or the second sensor 124, are generally known in the art as any apparatus operable to detect or measure a physical phenomenon or property, and generally provide a signal indicative of the phenomenon or property that is detected or measured. For example, the first sensor 120 and the second sensor 124 may be configured to measure one or more operating parameters of the therapy system 100. In some embodiments, the first sensor 120 may be a transducer configured to measure pressure in a pneumatic pathway and convert the measurement to a signal indicative of the pressure measured. In some embodiments, for example, the first sensor 120 may be a piezoresistive strain gauge. The second sensor 124 may optionally be configured to measure operating parameters of the negative-pressure source 104, such as the voltage or current, in some embodiments. Preferably, the signals from the first sensor 120 and the second sensor 124 are suitable as an input signal to the controller 110, but some signal conditioning may be appropriate in some embodiments. For example, the signal may need to be filtered or amplified before it can be processed by the controller 110. Typically, the signal is an electrical signal that is transmitted and/or received on by wire or wireless means, but may be represented in other forms, such as an optical signal.

The solution source 114 is representative of a container, canister, pouch, bag, or other storage component, which can provide a solution for instillation therapy. Compositions of solutions may vary according to a prescribed therapy. Examples of therapeutic solutions that may be suitable for some prescriptions include hypochlorite-based solutions, silver nitrate (0.5%), sulfur-based solutions, biguanides, cationic solutions, and isotonic solutions. In one illustrative embodiment, the solution source 114 may include a storage component for the solution and a separate cassette for holding the storage component and delivering the solution to the tissue site 150, such as a V.A.C. VeraLink™ Cassette available from Kinetic Concepts, Inc. of San Antonio, Texas.

The container 112 may also be representative of a container, canister, pouch, or other storage component, which can be used to collect and manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy. In some embodiments, the container 112 may comprise a canister having a collection chamber, a first inlet fluidly coupled to the collection chamber and a first outlet fluidly coupled to the collection chamber and adapted to receive negative pressure from a source of negative pressure. In some embodiments, a first fluid conductor may comprise a first member such as, for example, the conduit 128 fluidly coupled between the first inlet and the tissue interface 108 by the negative-pressure interface, and a second member such as, for example, the conduit 126 fluidly coupled between the first outlet and a source of negative pressure whereby the first conductor is adapted to provide negative pressure within the collection chamber to the tissue site.

The therapy system 100 may also comprise a flow regulator such as, for example, a regulator 118 fluidly coupled to a source of ambient air to provide a controlled or managed flow of ambient air to the sealed therapeutic environment provided by the dressing 102 and ultimately the tissue site. In some embodiments, the regulator 118 may control the flow of ambient fluid to purge fluids and exudates from the sealed therapeutic environment. In some embodiments, the regulator 118 may be fluidly coupled to the tissue interface 108 through the dressing interface 107. The regulator 118 may be configured to fluidly couple the tissue interface 108 to a source of ambient air. In some embodiments, the regulator 118 may be disposed within the therapy system 100 rather than being proximate to the dressing 102 so that the air flowing through the regulator 118 is less susceptible to accidental blockage during use. In such embodiments, the regulator 118 may be positioned proximate the container 112 and/or proximate a source of ambient air, where the regulator 118 is less likely to be blocked during usage.

Figure 2:
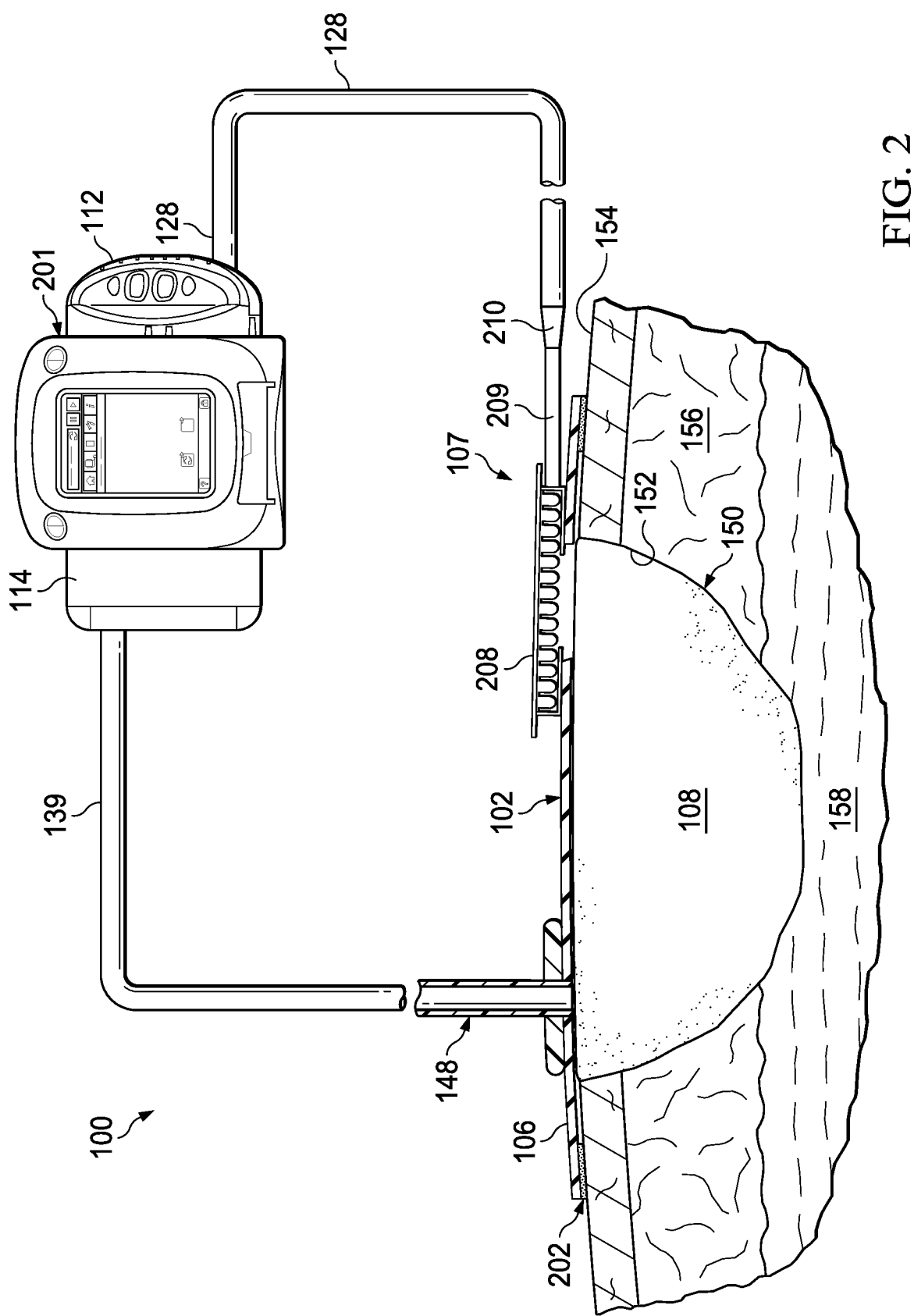
FIG. 2 is a schematic diagram of an example embodiment of the therapy system of FIG. 1 applied to a tissue site.

FIG. 2 is a schematic diagram of an example embodiment of the therapy system 100 configured to apply negative pressure and treatment solutions to a tissue site 150. Some components of the therapy system 100 may be housed within or used in conjunction with other components, such as processing units, alarm indicators, memory, databases, software, display devices, or user interfaces that further facilitate therapy. For example, in some embodiments, the negative-pressure source 104 may be combined with the controller 110 and other components into a therapy unit, such as a therapy unit 201 illustrated in FIG. 2. The therapy unit 201 may be, for example, a V.A.C. ULTA™ Therapy Unit available from Kinetic Concepts, Inc. of San Antonio, Texas.

In operation, the tissue interface 108 may be placed within, over, on, or otherwise proximate a tissue site, such as tissue site 150. The cover 106 may be placed over the tissue interface 108 and an attachment device 202 can seal the cover 106 to an attachment surface near the tissue site 150. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site 150 through the tissue interface 108 in the sealed therapeutic environment can induce macrostrain and microstrain in the tissue site, as well as remove exudates and other fluids from the tissue site, which can be collected in container 112.

In the example of FIG. 2, the therapy system 100 is presented in the context of a tissue site that includes a wound 152, which is through the epidermis 154, or generally skin, and the dermis 156 and reaching into a hypodermis, or subcutaneous tissue 158. The therapy system 100 may be used to treat a wound of any depth, as well as many different types of wounds, including open wounds, incisions, or other tissue sites. Treatment of the tissue site 150 may include removal of fluids originating from the tissue site 150, such as exudates or ascites, or fluids instilled into the dressing to cleanse or treat the tissue site 150, such as antimicrobial solutions.

The dressing interface 107 of FIG. 2 is substantially flat and flexible, but also compressible without occluding or blocking the fluid pathway between the conduit 128 and the tissue interface 108. In some embodiments, the dressing interface 107 may comprise an applicator 208 adapted to be positioned in fluid communication with the tissue interface 108. A bridge 209 can be fluidly coupled to the applicator 208 and extend to an adapter 210. The bridge 209 may have a substantially flat profile, and the adapter 210 may be configured to fluidly couple the bridge 209 to a tube or other round fluid conductor, such as the conduit 128 illustrated in the example of FIG. 2. In some embodiments, the adapter 210 may have one or more sealing valves, which can isolate the conduit 128 if separated from the dressing interface 107. In some embodiments, the dressing interface 107, including both the applicator 208 and the bridge 209, may have a length that can vary between about 15 cm to about 30 cm. In some embodiments, the applicator 208 and the bridge 209 may be formed as a single device as shown. In other embodiments, the applicator 208 and the bridge 209 may be separate components that are coupled together to form a single device. In yet other embodiments, the applicator 208 and the bridge 209 may be separate components that may be used independently of each other as a single component in the therapy system 100.

Figure 3:
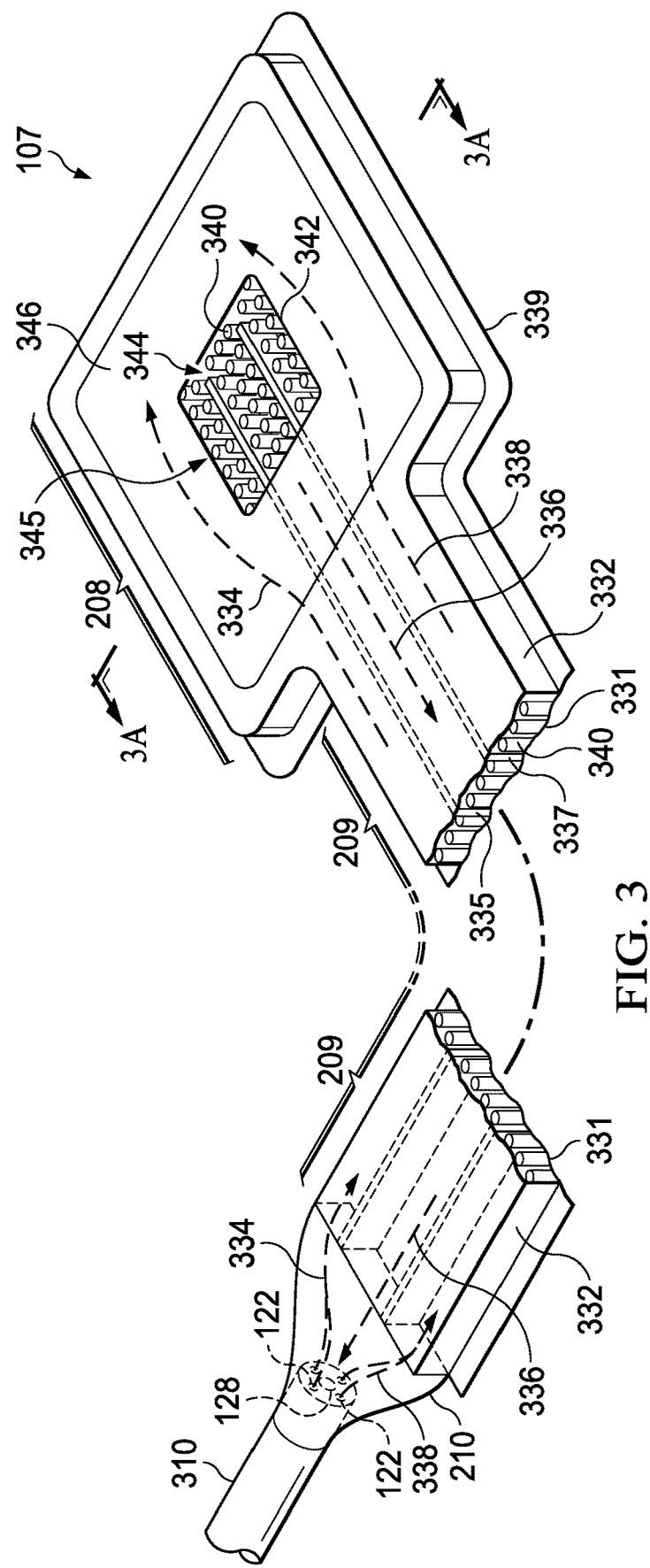
FIG. 3 is a segmented perspective view of an example dressing interface having a low profile structure that may be associated with some embodiments of the therapy system of FIG. 1.

FIG. 3 is a segmented perspective bottom view of an example of the dressing interface 107, illustrating additional details that may be associated with some embodiments. The dressing interface 107 of FIG. 3 generally has a low profile structure. FIG. 3 further illustrates features that may be associated with some embodiments of the applicator 208 and the bridge 209 of FIG. 2. The applicator 208 may be bulbous or any shape suitable for applying therapy to the tissue interface 108, depending on the size and nature of the tissue site 150. The bridge 209 in the example of FIG. 3 is generally long and narrow. An adapter, such as the adapter 210, may fluidly couple the bridge 209 to a fluid conductor, such as the conduit 128. In some examples, the conduit 128 and the conduit 122 may be combined in a conduit 310, as illustrated in the example of FIG. 3. For example, the conduit 310 may be a multi-lumen tube in which a central lumen corresponds to the conduit 128 and one or more peripheral lumens corresponds to the conduit 122. The other end of the conduit 310 may be fluidly coupled to the negative-pressure source 104 and the first sensor 120 either directly or indirectly through the container 112.

In some example embodiments, the applicator 208 and the bridge 209 may comprise a top layer such as, for example, a first layer 331, and a base layer such as, for example, a second layer 332. The second layer 332 may be coupled to the first layer 331 around the periphery of the first layer 331 to form an enclosed space within the dressing interface 107. The enclosed space may be formed between the first layer 331 and the second layer 332 of both the applicator 208 and the bridge 209. In some examples the enclosed space may be sealed along the periphery of the applicator 208, the bridge 209, or both. The first layer 331 and the second layer 332 may both be formed from or include a polymeric film. The first layer 331 and the second layer 332 may be coupled around the periphery of the dressing interface 107 to form the enclosed space by welding (RF or ultrasonic), heat sealing, or adhesive bonding such as, for example, acrylics or cured adhesives. For example, the first layer 331 and the second layer 332 may be welded together around the periphery of the dressing interface 107 and may form a flange 339 around the periphery of the dressing interface 107 as a result of the weld. One skilled in the art would understand that there are a variety of methods for coupling the first layer 331 and the second layer 332 to form the enclosed space within the dressing interface 107.

The dressing interface 107 of FIG. 3 may further comprise at least one barrier or wall, such as a first wall 335, between the first layer 331 and the second layer 332. In some embodiments, the first wall 335 may extend from the end of the bridge 209 adjacent the adapter 210 into the applicator 208 to form at least two enclosed spaces or fluid pathways between the first layer 331 and the second layer 332 within the dressing interface 107. In some examples, the dressing interface 107 may further comprise a second barrier, such as a second wall 337, between the first layer 331 and the second layer 332. In some embodiments, the second wall 337 also may extend from the end of the bridge 209 adjacent the adapter 210 into the applicator 208. In some example embodiments, the wall 335 and the wall 337 may comprise a polymeric film coupled between the first layer 331 and the second layer 332. In some other example embodiments, the wall 335 and the wall 337 may comprise a weld (RF or ultrasonic), a heat seal, an adhesive bond, or a combination of any of the foregoing. In those embodiments comprising two walls, e.g., the first wall 335 and the second wall 337, such embodiments may form three enclosed spaces or fluid pathways within the enclosed space between the first layer 331 and the second layer 332. In some embodiments, two of the fluid pathways may be dedicated to measuring pressure. For example, a first pressure-sensing pathway 334 and a second pressure-sensing pathway 338 (as indicated by the dashed line arrows) in the example of FIG. 3 may be configured as feedback pathways. A third fluid pathway, such as a negative-pressure pathway 336, may be utilized for providing negative pressure.

In some example embodiments, the first pressure-sensing pathway 334, the negative-pressure pathway 336, and the second pressure-sensing pathway 338 may be fluidly coupled to the conduit 310 by the adapter 210. For example, the negative-pressure pathway 336 may be fluidly coupled to the conduit 128 so that the negative-pressure pathway 336 functions to deliver negative pressure to the tissue interface 108. The first pressure-sensing pathway 334 and the second pressure-sensing pathway 338 may be fluidly coupled to the conduit 122. In other embodiments, the first pressure-sensing pathway 334 and the second pressure-sensing pathway 338 both may be fluidly coupled to a single space within the adapter 210 that is also fluidly coupled to the conduit 122. In some example embodiments, the other end of the first pressure-sensing pathway 334, the negative-pressure pathway 336, and the second pressure-sensing pathway 338 may terminate within the applicator 208 of the dressing interface 107 and be fluidly coupled to each other within the applicator 208 for delivering and sensing the negative pressure associated with the tissue interface 108.

The applicator 208 may comprise an opening or aperture 342 in the second layer 332, adapted to fluidly couple the enclosed space of the dressing interface 107 to the tissue interface 108. The aperture 342, along with the first layer 331 and the second layer 332 portions of the applicator 208 may define a recessed space 344 within the enclosed space of the applicator 208, wherein the recessed space 344 is adapted to be in fluid communication with the tissue interface 108 in use. The portion of the recessed space 344 covered by the second layer 332 of the applicator 208 may be referred to as a covered space. In some example embodiments, the walls 335 and 337 may extend only partially into the recessed space 344 so that the end of the walls 335 and 337 are exposed by the aperture 342 as shown in FIG. 3. In this embodiment, the first pressure-sensing pathways 334 and the second pressure-sensing pathway 338 are in fluid communication with the recessed space 344. The negative-pressure pathway 336 is also in fluid communication with the recessed space 344 and can be adapted to deliver negative pressure to the tissue interface 108 through the recessed space 344. In some example embodiments (not shown), the walls 335 and 337 may extend beyond the aperture 342 so that less of the first pressure-sensing pathway 334 and the second pressure-sensing pathway 338 are being exposed to negative pressure being delivered to the tissue interface 108 by the negative-pressure pathway 336 to avoid occlusions and/or blockages from the tissue site 150.

The dressing interface 107 may further comprise a plurality of features, such as flexible projections, flexible standoffs, or closed cells. For example, closed cells 340 illustrated in the example of FIG. 3 may be generally characterized as bubbles that have a bottom portion extending from the first layer 331 and a top portion extending within the enclosed spaces toward the second layer 332 outside the recessed space 344. Within the recessed space 344, the top portion of the closed cells 340 extending from the first layer 331 may extend toward the tissue interface 108 and may be adapted to come in direct contact with the tissue interface 108 in use, or may be positioned above the tissue interface 108. Features such as the closed cells 340 can provide a cushion to help prevent the enclosed spaces of the dressing interface 107 from collapsing as a result of external forces. In some example embodiments, the top portion of the closed cells 340 may come in contact with the second layer 332, and in some other example embodiments, the top portion of the closed cells 340 may be coupled to the second layer 332. In some example embodiments, the closed cells 340 may be disposed in the applicator 208 but not in the bridge 209, which may contain, for example, a fabric material instead of the closed cells 340. In some example embodiments, the features may comprise projections or nodes (not shown) having a flexibility similar to the closed cells 340.

The dressing interface 107 of FIG. 3 may also comprise an affixation surface 346 surrounding the aperture 342 in the applicator 208 of the second layer 332 that can be used to couple the dressing interface 107 to a tissue site. In some embodiments, a top drape (not shown) may be utilized to cover the applicator 208 to provide additional protection and support over the applicator 208 when the dressing interface 107 is applied to a tissue site. In some embodiments, a top drape may also be utilized to cover any adhesive that might be exposed from applying the dressing interface 107 to the tissue site. In some embodiments, a top drape may be similar to the cover 106. For example, a top drape may comprise or consist of a polymer, such as a polyurethane film.

Figure 3A:
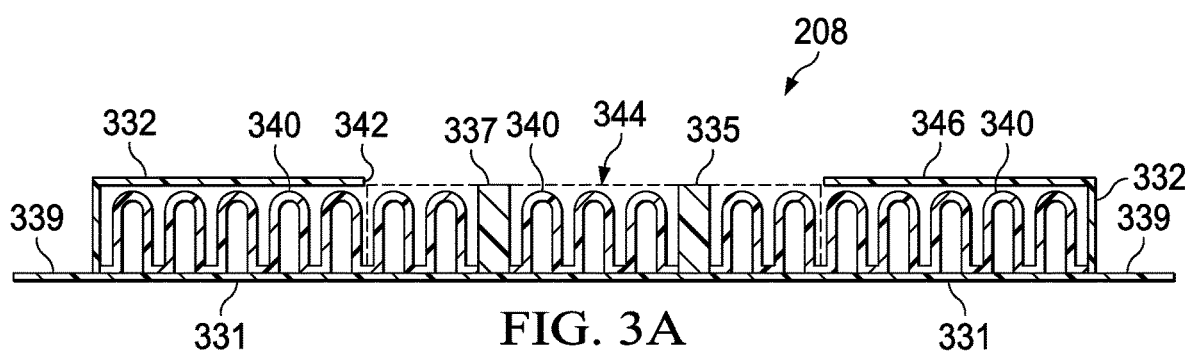
FIG. 3A is a section view of the dressing interface of FIG. 3.

FIG. 3A is a section view of the applicator 208 of FIG. 3, taken along line 3A-3A, illustrating additional details that may be associated with some embodiments. For example, the top portion of the closed cells 340 may extend from the first layer 331 toward the tissue interface 108 through the aperture 342 of the second layer 332 as illustrated in FIG. 3A. At least some of the closed cells 340 may be configured to come in direct contact with the tissue interface 108 through the aperture 342.

Figure 3B:
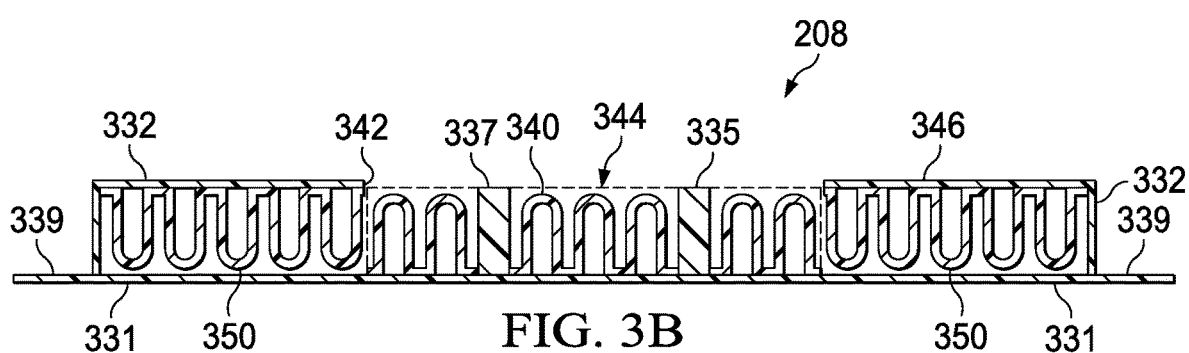
FIG. 3B is a section view of another example of a dressing interface.

FIG. 3B is a section view of another example of the applicator 208, illustrating details that may be associated with some embodiments. In the example of FIG. 3B, the applicator 208 may further comprise a plurality of features or closed cells extending from the second layer 332 toward the first layer 331. The top portions of the closed cells 340 may still extend from the first layer 331 into the recessed space 344.

Figure 3C:
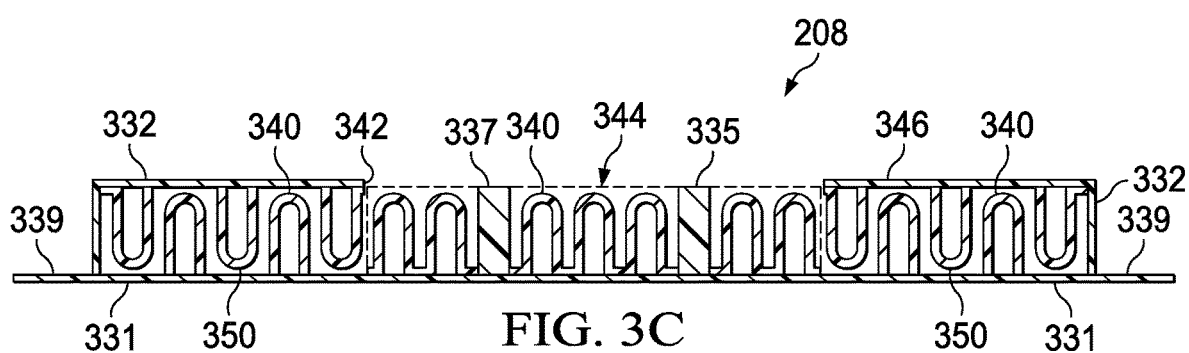
FIG. 3C is a section view of another example of a dressing interface.

FIG. 3C is a section view of another example of the applicator 208. In the example of FIG. 3C, the applicator 208 comprises both a plurality of closed cells 340 and a plurality of closed cells 350 extending from the first layer 331 and the second layer 332, respectively, within the enclosed spaces outside the recessed space 344 toward the second layer 332 and the first layer 331, respectively. Within the recessed space 344, the top portions of the closed cells 340 may extend from the first layer 331 into the recessed space 344.

In some example embodiments, the first layer 331 and the second layer 332, including the closed cells 340 and the closed cells 350, respectively, may be formed from a non-porous, polymeric film that may comprise any flexible material that can be manipulated to enclose closed cells, including various thermoplastic materials, e.g., polyethylene homopolymer or copolymer, polypropylene homopolymer or copolymer, etc. Non-limiting examples of suitable thermoplastic polymers include polyethylene homopolymers, such as low density polyethylene (LDPE) and high density polyethylene (HDPE), and polyethylene copolymers such as, e.g., ionomers, EVA, EMA, heterogeneous (Zeigler-Natta catalyzed) ethylene/alpha-olefin copolymers, and homogeneous (metallocene, single-cite catalyzed) ethylene/alpha-olefin copolymers. Ethylene/alpha-olefin copolymers are copolymers of ethylene with one or more comonomers selected from $C_3$ to $C_{20}$ alpha-olefins, such as 1-butene, 1-pentene, 1-hexene, 1-octene, methyl pentene and the like, in which the polymer molecules comprise long chains with relatively few side chain branches, including linear low density polyethylene (LLDPE), linear medium density polyethylene (LMDPE), very low density polyethylene (VLDPE), and ultra-low density polyethylene (ULDPE). Various other materials are also suitable such as, e.g., polypropylene homopolymer or polypropylene copolymer (e.g., propylene/ethylene copolymer), polyesters, polystyrenes, polyamides, polycarbonates, etc.

In some example embodiments, the first layer 331 and the second layer 332, including the closed cells 340 and the closed cells 350, respectively, may comprise a polymeric film such as, for example, a thermoplastic polyurethane (TPU) film that is permeable to water vapor but impermeable to liquid. The first layer 331 and the second layer 332 may be in various degrees breathable and may have MVTRs which are proportional to their thickness. For example, the MVTR may be at least 300 $g/m^2$ per twenty-four hours in some embodiments. For permeable materials, the permeability generally should be low enough to maintain a desired negative pressure for the desired negative therapy treatment.

In some example embodiments, the layer having the closed cells may be formed from two sheets of polymeric film having inner surfaces coupled together to form sealed regions defining the plurality of closed cells. If the dressing interface 107 is positioned at the tissue site and negative pressure is applied as described above, the closed cells formed by the polymeric film are structured so that they do not completely collapse from apposition forces resulting from the application of negative pressure and/or external forces to the dressing interface 107 and the tissue site. The two sheets of polymeric film may be a single sheet of material having two laminae or two separate sheets that are coupled together to form the closed cells. The sheets of polymeric film may initially be separate sheets that are brought into superposition and sealed or they may be formed by folding a single sheet unto itself with a heat-sealable surface facing inward. Each sheet of the polymeric film also may be a monolayer or multilayer structure, depending on the application or the desired structure of the closed cells.

In some embodiments, the polymeric film may possess sufficient tensile strength to resist stretching under apposition forces created by negative pressure therapy. The tensile strength of a material is the ability of material to resist stretching as represented by a stress-strain curve where stress is the force per unit area, i.e., pascals (Pa), newtons per square meter (N/m²), or pounds per square inch (psi). The ultimate tensile strength (UTS) is the maximum stress the material can withstand while being stretched before failing or breaking. Many materials display a linear elastic behavior defined by a linear stress-strain relationship often extending up to a nonlinear region represented by the yield point, i.e., the yield strength of a material. For example, high density polyethylene (HDPE) has a high tensile strength and low-density polyethylene (LDPE) has a slightly lower tensile strength, which are suitable materials for the sheets of non-porous, polymeric film as set forth above. Linear low density polyethylene (LLDPE) is often used as well because the material stretches very little as the force is increased up to the yield point of the material. Thus, the closed cells are able to resist collapsing (or stretching) when subjected to an external force or pressure. For example, HDPE has a UTS of about 37 MPa and may have a yield strength that ranges from about 26-33 MPa depending on the thickness of the material, while LDPE has somewhat lower values.

In some example embodiments, the first layer 331 and the second layer 332, including the closed cells 340 and the closed cells 350, respectively, may comprise a thermoplastic polyurethane (TPU) film as described above. The thermoplastic polyurethane film may be, for example, a Platilon® thermoplastic polyurethane film available from Convestro LLC, which may have a UTS of about 60 MPa and may have a yield strength of approximately 11 MPa or greater than about 10 MPa depending on the thickness of the material. Therefore, in some example embodiments, it is desirable that the non-porous, polymeric film may have a yield strength greater than about 10 MPa, depending on the type and thickness of material. A material having a lower yield strength may be too stretchable and, therefore, more susceptible to breaking with the application of small amounts of compression and/or apposition forces.

Figure 4:
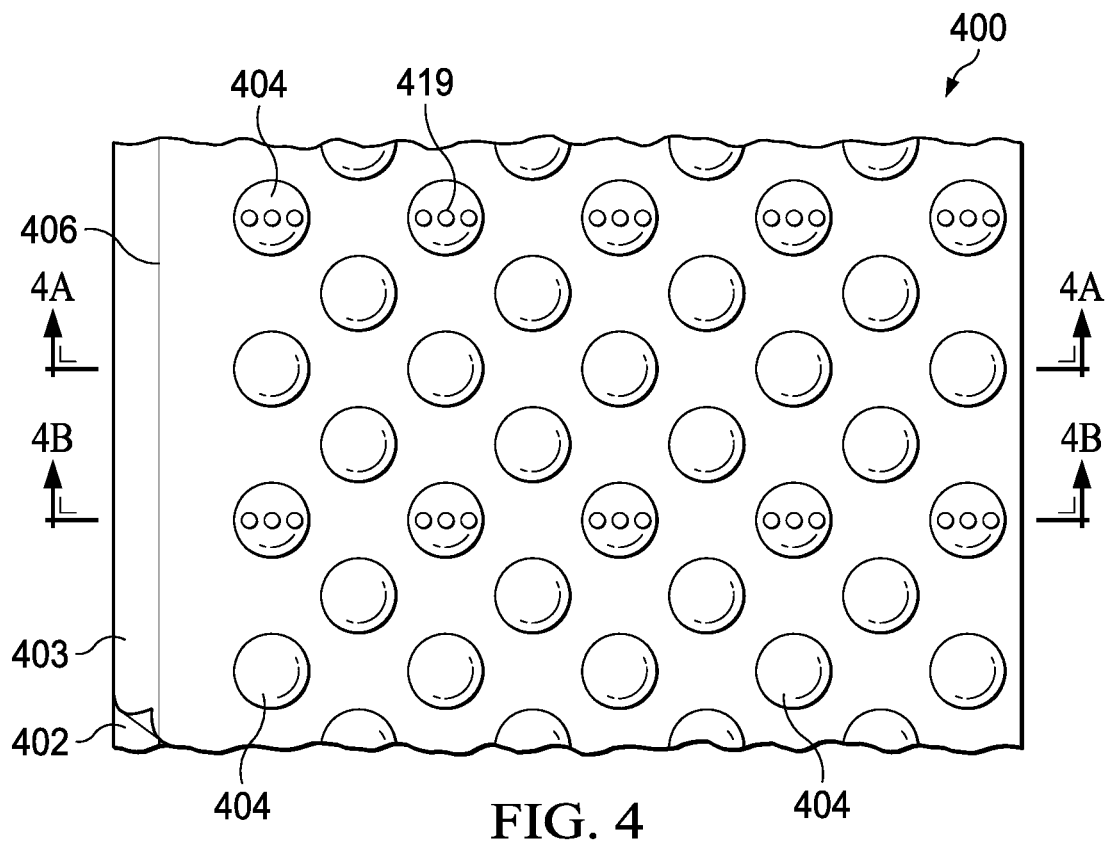
FIG. 4 is a top view of a layer illustrating features that may be associated with some embodiments of the dressing interface of FIG. 3.

FIG. 4 is a top view a layer 400 that may be illustrative of features that may be associated with various examples of the first layer 331, the second layer 332, or both. In some example embodiments, the layer 400 may comprise two sheets of polymeric film, such as a sheet 402 and a sheet 403. The sheet 403 may have a plurality of blisters 404 in some embodiments. For example, the blisters 404 may comprise raised formations having closed ends that extend above or below a plane of the sheet 403. Within each of the blisters 404 may be an empty cavity, which may be open to the surrounding environment. In some examples, the blisters 404 may be vacuum-formed regions of the sheet 403.

A portion of each of the sheet 402 and the sheet 403 may have inner surfaces coupled to each other to form a sealed region 406. The sealed region 406 may extend between all or substantially all of the blisters 404 to define a plurality of closed cells 407, or may extend between a group of the blisters 404 to define a group of the closed cells 407 that may be in fluid communication with each other. The sheet 402 may also cover the blisters 404 to form the closed cells 407. In some embodiments, the sheet 402 and the sheet 403 may be attached to one another at their lateral edges such that all of the blisters 404 are in fluid communication which each other.

In some embodiments, the sealed region 406 may be formed by a heat seal between the inner surfaces of the sheets 402 and 403, while the blisters 404 may be formed simultaneously by vacuum forming. In another example embodiment, the sealed region 406 may be formed by adhesion between the sheet 402 and the sheet 403. Alternatively, the sheet 402 and the sheet 403 may be adhesively bonded to each other. The sealed region 406 may be flexible enough so that the dressing interface 107 is sufficiently flexible to conform to the shape the tissue site. The sealed region 406 may be sufficiently flexible or sized so that the dressing interface 107 may be folded to conform to a tissue site to provide optimal negative pressure to the tissue site.

In some example embodiments, the closed cells 407 may be substantially airtight to inhibit collapsing of the closed cells 407 from the application of negative pressure, which could block the flow of fluid through the dressing interface 107. The closed cells 407 may be substantially airtight when formed and have an internal pressure that is an ambient pressure. In another example embodiment, the closed cells 407 may be inflated with air or other suitable gases such as, for example, carbon dioxide or nitrogen. The closed cells 407 may be inflated to have an internal pressure greater than the atmospheric pressure to maintain their shape and resistance to collapsing under pressure and external forces. For example, the closed cells 407 may be inflated to a pressure up to about 25 psi above the atmospheric pressure.

The sheet 402 and the sheet 403 may have a thickness within a range of 400 to 600 microns. In some example embodiments, the first layer 331 and the second layer 332, including the closed cells 340 and the closed cells 350 respectively, may be formed from thermoplastic polyurethane film having a thickness of about 500 microns. In some example embodiments, the sheet 402 and the sheet 403, prior to fabricating either one of the first layer 331 or the second layer 332, may each have a thickness of about 200 μm to about 600 μm. In some embodiments, the sheet 402 and the sheet 403 may each have a thickness of about 250 μm. In some other embodiments, the sheet 402 and the sheet 403 may each have a thickness of about 500 μm.

In some embodiments, the thickness of a layer that does not have closed cells may be up to 50% thinner than the thickness of the layer that that includes closed cells. For example, referring to FIG. 3A, the thickness of the second layer 332 without any closed cells may be up to 50% thinner than the thickness of the first layer 331 that has the closed cells 340. After the layers have been fabricated, the sealed region 406 may have a thickness between about 800 μm and about 1200 μm. If the fabrication process comprises injection molding, the blisters 404 may have a thickness between about 400 μm and about 500 μm. However, if the blisters 404 are fabricated by drawing the film, the top portion of the blisters 404 may have a thickness as thin as 50 μm.

After the blisters 404 have been fabricated, the walls of the blisters 404 may have a thickness relative to the thickness of the individual sheets 402 and 403 as defined by a draw ratio, i.e., the ratio of the average height of the blisters 404 to the average thickness of the sheets 402 and 403. In some example embodiments, the blisters 404 may have a generally tubular shape, which may have been formed from the sheets 402 and 403 having various thicknesses and draw ratios. In some example embodiments, the sheets 402 and 403 may have an average thickness of 500 μm and the blisters 404 may have an average height in a range between about 2.0 mm and 5.0 mm. Consequently, the blisters 404 may have a draw ratio ranging from about 4:1 to about 10:1 for heights of 2.0 and 5.0 mm, respectively. In another example embodiment, the draw ratio may range from about 5:1 to about 13:1 where the thickness of the sheets 402 and 403 is an average of about 400 μm. In yet another example embodiment, the draw ratio may range from about 3:1 to about 9:1 where the thickness of the sheets 402 and 403 is an average of about 600 μm. In some embodiments, the blisters 404 may have an average height in a range between about 1.0 mm and 4.0 mm, depending on the thickness of the sheets 402 and 403. The sheets 402 and 403 may each have the same or different thicknesses and flexibilities, but are substantially non-stretchable as described above so that the closed cells 407 maintain a generally constant volume without bursting after a compression force is applied to the dressing interface 107 or negative pressure is applied to the dressing interface 107 and the tissue site. Consequently, even when a load is applied to the dressing interface 107, which squeezes the closed cells 407 into a different shape, the closed cells 407 are sufficiently flexible to recover their original shape after being squeezed without bursting.

The open ends of the blisters 404 may define the cross-sectional shape of the closed cells 407 as being generally circular as shown, but in other embodiments the blisters 404 may be a rectangular or triangular shape, hexagonal, or other geometric or an irregular shape.

Figure 4A:
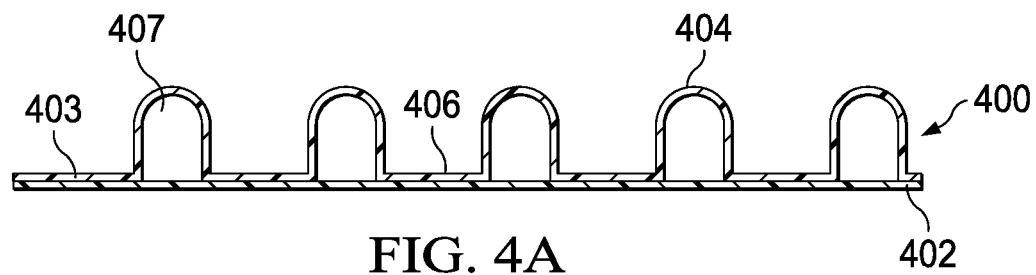
FIG. 4A is a section view of the layer of FIG. 4.

FIG. 4A is a section view of the layer 400 taken along line 4A-4A of FIG. 4, illustrating additional details that may be associated with some examples. In some embodiments, the blisters 404 may be hemispherical, as illustrated in the example of FIG. 4A. In other example embodiments, the blisters 404 may be conical, cylindrical, tubular having a flattened or hemispherical end, or geodesic. These shapes may be formed in either one of the sheets 402 and 403, such as the tubular shape of the blisters 404 shown in FIG. 4A. The blisters 404 may be tubular shapes formed with generally parallel walls extending from the sealed region 416 to a hemispherical or flat top portion of the blisters 404. Alternatively, the walls of the blisters 404 may taper or expand outwardly from the sealed region 416 to the top portion so that the diameter of the top portion of the closed cells 407 is larger than at the base of the closed cells 407.

In some embodiments, the blisters 404 that are generally hemispherical or tubular in shape may have a diameter between about 1.0 mm and about 10 mm. In some other embodiments, the blisters 404 may have a diameter between about 2.0 mm and about 5.0 mm. In some embodiments, the blisters 404 also may have a pitch, i.e., the center to center distance between each of the blisters 404, between about 1 mm and 10 mm. In some other embodiments, the blisters 404 may also have a pitch between about 2 mm and about 3 mm. The surface area of the layer 400 covered by the closed cells 407 may also be determined as a percentage, i.e., the cell coverage percentage. In one example embodiment wherein the diameter of each of the blisters 404 is about 1.0 mm and the pitch is about 2.0 mm, the cell coverage percentage is about 22% of the surface area of the layer 400. In another example embodiment wherein the diameter of each of the blisters 404 is about 2.0 mm and the pitch is about 5.0 mm, the cell coverage percentage is about 14% of the surface area of the layer 400. In yet another example embodiment wherein the diameter of each of the blisters 404 is about 1.5 mm, the pitch is about 2.0 mm, and the blisters 404 are more tightly arranged such that there are about 28.5 cells in a 10 mm² section of the layer 400, the cell coverage percentage is about 51% of the surface area of the layer 400. Depending on the diameter, pitch, and arrangement of the closed cells 407, the cell coverage percentage may range between about 10% and about 60% of the surface area of either one of the layers having the closed cells such as layer 400. Blisters 404 having other shapes also may have a cell coverage percentage in generally the same range.

When the dressing interface 107 is disposed at the tissue site, a portion of the closed cells 340 may extend through the recessed space 344 and the aperture 342 of the dressing interface 107 to contact the tissue interface 108. A portion of the closed cells 340 extending through the recessed space 344 may be textured with surface features, which may be protrusions or indentations, to enhance fluid flow through the dressing interface 107 to the tissue interface 108 and the tissue site.

Figure 4B:
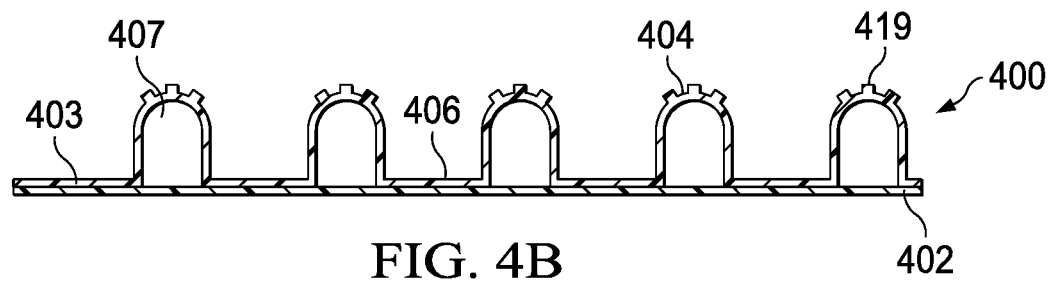
FIG. 4B is a section view of another example of the layer of FIG. 4.

FIG. 4B is a section view of the layer 400 of FIG. 4 taken along line 4B-4B, illustrating additional details that may be associated with some examples. In the example of FIG. 4B, one or more of the blisters 404 are embossed with projections or nodes, such as the nodes 419. The nodes 419 can be configured to contact the tissue interface 108 to enhance fluid flow to a tissue site. The nodes 419 may be projections that are flexible or rigid. In some embodiments, the projections may be formed from a substantially gas impermeable material such as silicone. In other embodiments, the projections may be formed from a semi-gas permeable material. The projections may be formed as an integral part of the sheet 403, and, therefore, they may also be formed from the same material. In some embodiments, the projections may be solid, while in other embodiments the projections may be hollow to increase flexibility. The projections may form a plurality of channels and/or voids to distribute reduced pressure and allow for fluid flow among the projections. The projections may be dimensioned to provide local load points evenly distributed at the tissue interface 108. The pattern and position of the projections may be uniform or non-uniform. The projections may have different shapes, including, for example, the shape of a spike, cone, pyramid, dome, cylinder or rectangle.

The blisters 404 in adjacent rows or columns may be staggered in some examples, so that the cells may be nested together. In other embodiments, the blisters 404 may be arranged in other patterns suitable for the particular therapy being utilized. For example, the rows and columns of the blisters 404 may be arranged in line to form an aligned, rectangular pattern so that there is more spacing between the blisters 404. Increasing the spacing between the blisters 404 may increase fluid flow within the fluid pathways of the dressing interface 107, whereas a nested arrangement of closed cells may restrict fluid flow within the fluid pathways. Referring back to FIG. 3, for example, the closed cells 340 disposed in the negative-pressure pathway 336 are arranged in an aligned pattern that may increase fluid flow of negative pressure being applied to the tissue interface 108 to facilitate the removal of fluids and exudates within the recessed space 344. However, the closed cells 340 disposed in the pressure-sensing pathways 334 and 338 can be arranged in a nested pattern to facilitate pressure sensing within the recessed space 344 while impeding the inflow of fluids and exudates into the pressure-sensing pathways 334 and 338 to reduce the possibility of blockage.

In other example embodiments, the size and pitch of the closed cells also may be varied to effect change in the fluid flows through the fluid passageways. Referring again to FIG. 3, for example, the closed cells 340 disposed in the negative-pressure pathway 336 have a slightly larger diameter and pitch than the closed cells 340 disposed in the pressure-sensing pathways 334 and 338 that may increase fluid flow of negative pressure being applied to the tissue interface 108 to facilitate the removal of fluids and exudates within the recessed space 344. The closed cells 340 disposed in the pressure-sensing pathways 334 and 338 have a slightly smaller diameter and pitch that may restrict fluid flow to facilitate pressure sensing within the recessed space 344 while impeding the inflow of fluids and exudates into the sensing pathways 334 and 338 to avoid blockages.

Figure 5:
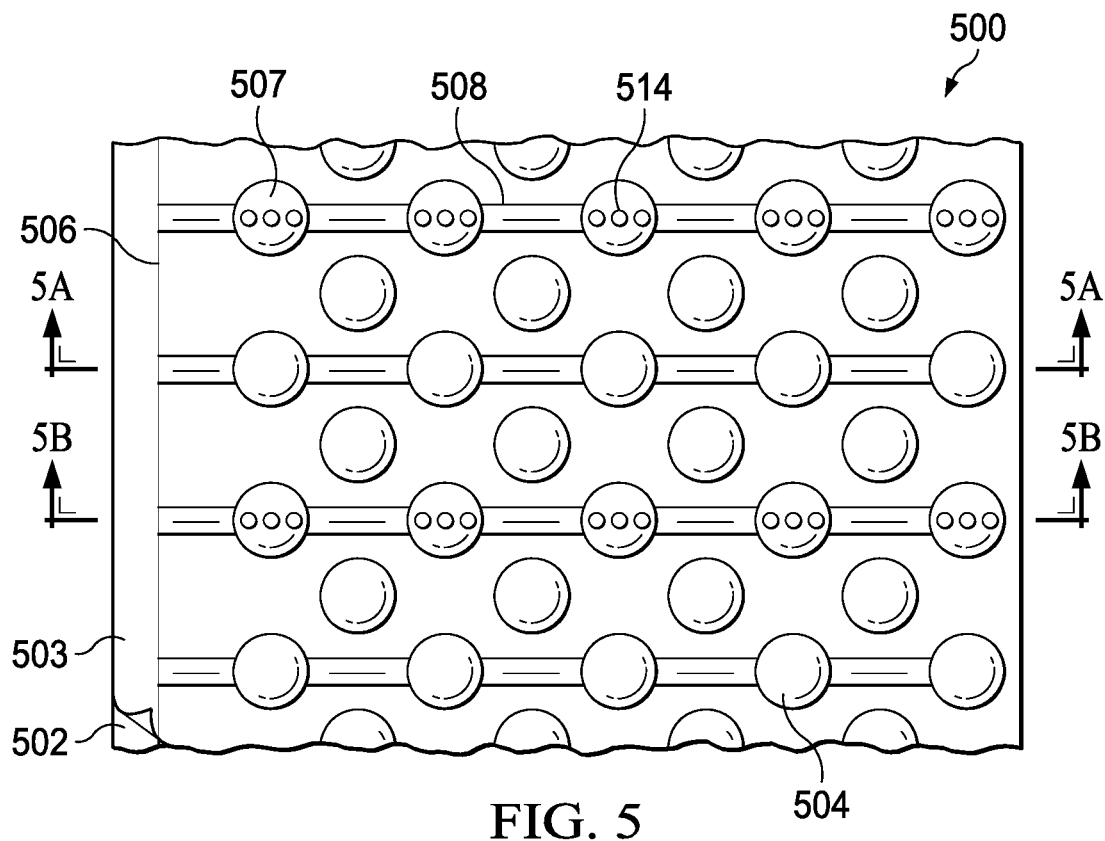
FIG. 5 is a top view of another example of a layer that may be associated with some embodiments of a dressing interface.

FIG. 5 is a top view of another example layer, illustrating certain features that may additionally or alternatively be associated with various examples of the first layer 331, the second layer 332, or both. For example, in FIG. 5 a layer 500 may comprise openings formed between closed cells to better distribute the apposition force applied to the layer 500 as a result of the application of negative pressure, because the volume of the chambers is greater than the volume of the individual closed cells. In some embodiments, the layer 500 may be similar in many respects to the layer 400, comprising two sheets 502 and 503 of polymeric film. The sheet 503 may have a plurality of blisters 504. The sheet 502 and the sheet 503 may have inner surfaces coupled to each other in a pattern defining a plurality of closed cells 507. The sheets 502 and 503 may be sealed to each other to form a sealed region 506 defining the closed cells 507. The layer 500 also may comprise a plurality of passageways 508 fluidly coupling at least two of the closed cells 507 to form a closed chamber. In some examples, a closed chamber may be formed by all of the closed cells 507 in a row fluidly coupled by the passageways 508 as shown in FIG. 5. The closed chambers may be formed in alternating rows as also shown in FIG. 5. The formation of closed chambers with closed cells in any pattern distributes apposition forces applied to the layer 500 more equally across the layer 500.

Figure 5A:
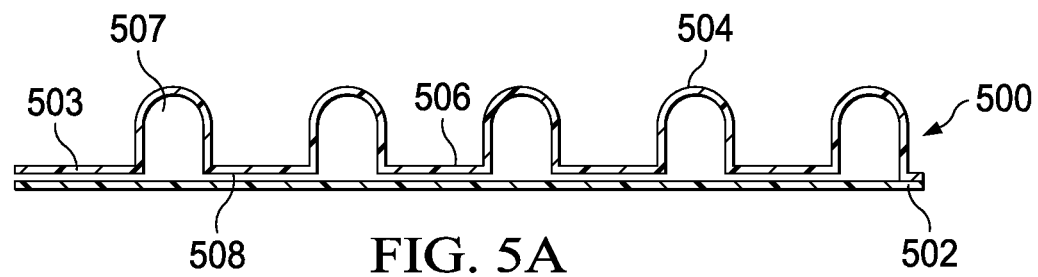
FIGS. 5A and 5B are cross-sectional views of the layer of FIG. 5.

FIG. 5A is a section view of the layer 500 taken along line 5A-5A, illustrating additional details that may be associated with some embodiments. For example, as seen in FIG. 5A, the closed cells 507 may be fluidly coupled through the passageways 508.

Figure 5B:
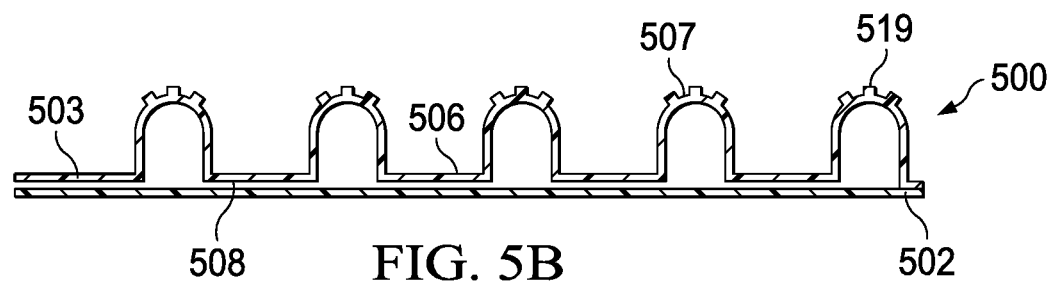

FIG. 5B is a section view of the layer 500 taken along line 5B-5B, illustrating additional details that may be associated with some embodiments. For example, one or more of the blisters 504 may be textured with surface features, which may be protrusions or indentations, to enhance fluid flow through the dressing interface 107. In some exemplary embodiments, as shown in FIG. 5B, one or more of the blisters 504 may be embossed with projections or nodes, such as the nodes 519, which can contact the tissue interface 108 to enhance fluid flow to a tissue site.

Figure 6:
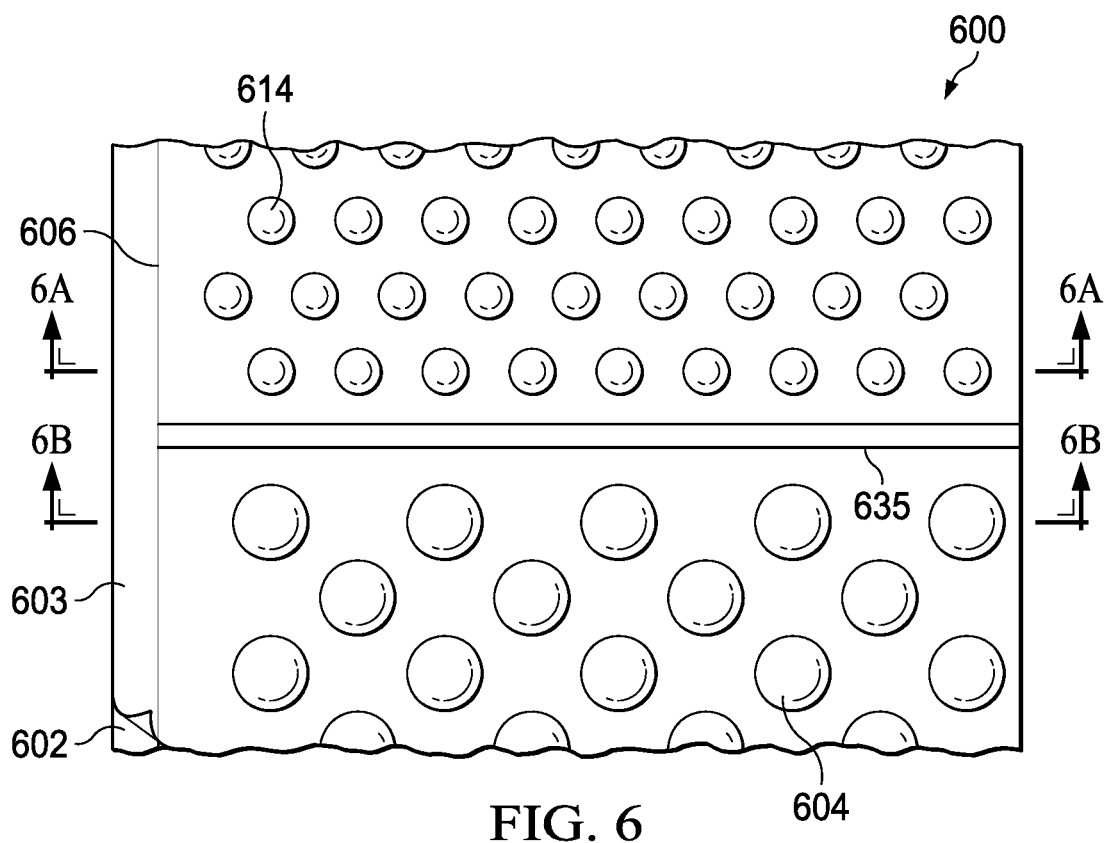
FIGS. 6, 6A, and 6B illustrate other examples of features that may be associated with the dressing interface of FIG. 3.
Figure 6A:
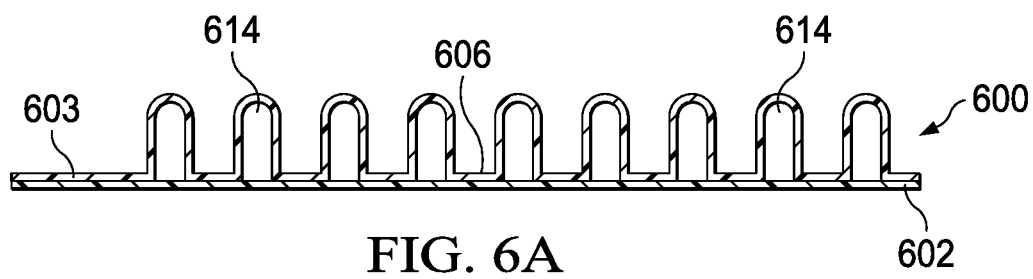
Figure 6B:
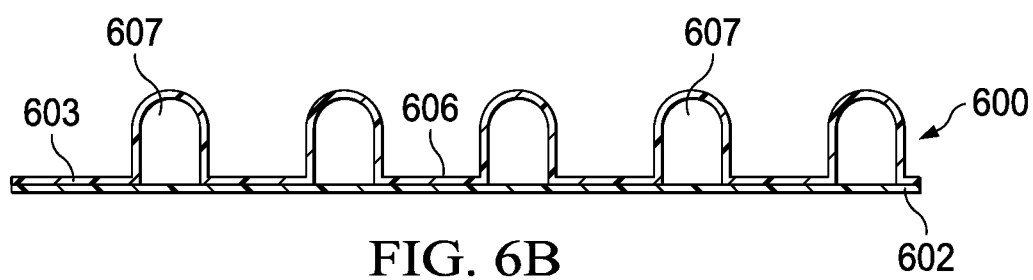

FIGS. 6, 6A, and 6B illustrate other examples of features that may be associated with the first layer 331, the second layer 332, or both. In FIG. 6, a closed-cell layer 600 also comprises two sheets 602 and 603 of polymeric film having inner surfaces sealed to each other in a pattern defining a plurality of closed cells in a nested arrangement including closed cells 607 and smaller closed cells 614. In some embodiments, a wall 635 similar to the first wall 335 shown in FIG. 3 may be disposed between the plurality of closed cells 607 and 614 forming the negative-pressure pathway 336 and the pressure-sensing pathway 334, respectively. As can be seen, the closed cells 607 disposed in the negative-pressure pathway 336 have a noticeably larger diameter and pitch than the smaller closed cells 614 that may increase fluid flow of negative pressure being applied to the tissue interface 108 to facilitate the removal of fluids and exudates within the recessed space 344. For example, the larger closed cells 607 may have a diameter in the range between about 1 mm and about 10 mm, whereas the smaller closed cells 614 may have a diameter in the range between about 1 mm and about 3 mm. The closed cells 614 disposed in the pressure-sensing pathway 334 have a noticeably smaller diameter and pitch than the larger closed cells 607 that may restrict fluid flow to facilitate pressure sensing within the recessed space 344 while impeding the inflow of fluids and exudates into the pressure-sensing pathway 334. It should be understood that the arrangement and dimensions of the closed cells may be tailored to manage the delivery of negative pressure to the tissue interface 108 and the measurement of pressure within the recessed space 344.

In operation, the tissue interface 108 may be placed within, over, on, or otherwise proximate a tissue site, such as the tissue site 150, as shown in the example of FIG. 2. The cover 106 may be placed over the tissue interface 108 and sealed to an attachment surface near the tissue site 150. For example, the cover 106 may be sealed to undamaged epidermis peripheral to a tissue site. The dressing 102 can provide a sealed therapeutic environment proximate to a tissue site, substantially isolated from the external environment, and the negative-pressure source 104 can reduce the pressure in the sealed therapeutic environment.

Figure 7:
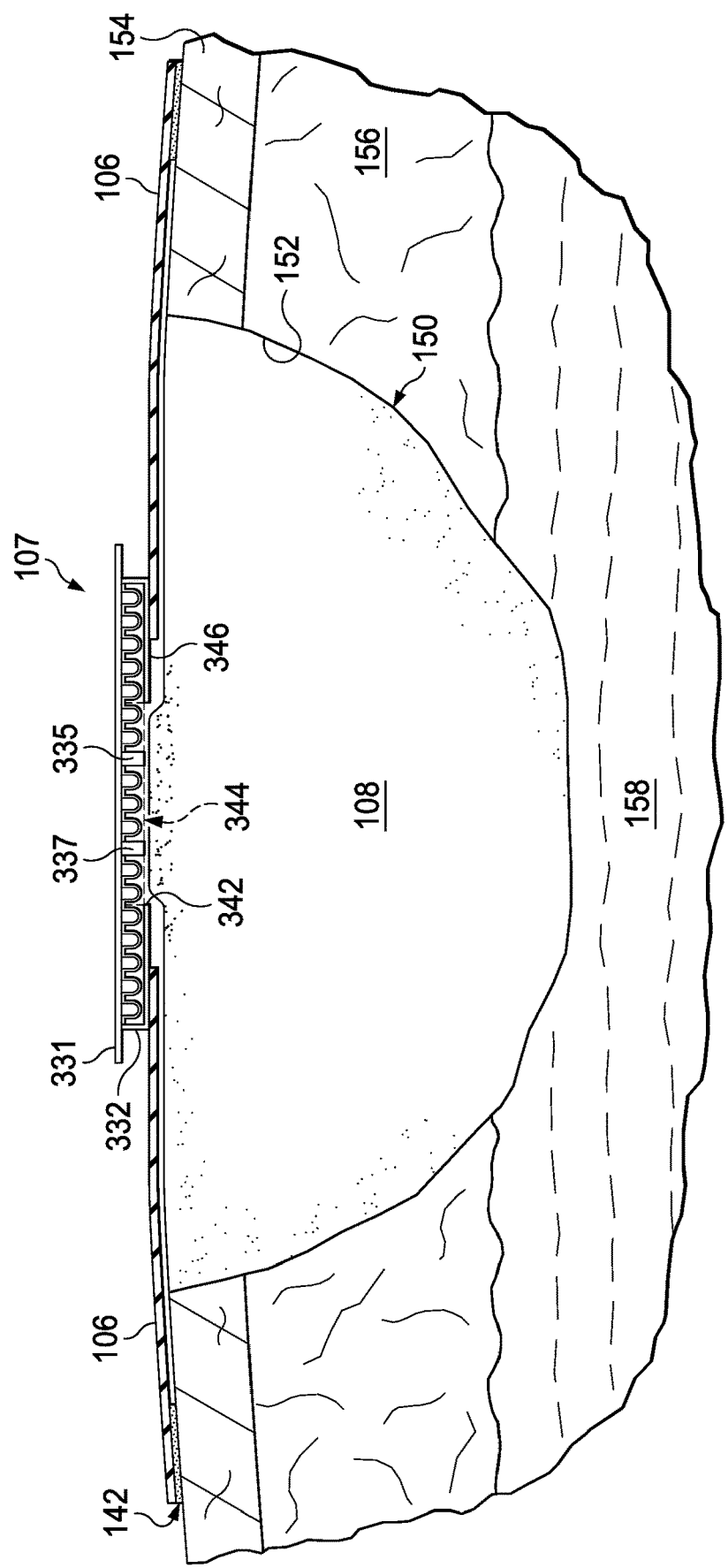
FIG. 7 is a schematic diagram of an example of the dressing interface of FIG. 3 applied to a tissue site.

FIG. 7 is a schematic diagram of the dressing interface 107 of FIG. 3 applied to the tissue site 150. The tissue interface 108 may be in fluid communication with the recessed space 344 through the aperture 342 of the dressing interface 107. The affixation surface 346 of the dressing interface 107 may be coupled to the cover 106 to seal and fluidly couple the recessed space 344 of the dressing interface 107 to the tissue interface 108. The first wall 335 and the second wall 337 form the three enclosed spaces or fluid pathways 334, 336 and 338 (as indicated by the dashed line arrows in FIG. 3) between the first layer 331 and the second layer 332 as described above.

Within the recessed space 344, the top portion of the closed cells 340 can extend from the first layer 331 toward the tissue interface and may be adapted to come in direct contact with the tissue interface 108 if negative pressure is applied to the dressing interface 107. If negative pressure is applied to the tissue interface 108, the dressing interface 107 can be compressed as a result of an apposition force that causes the first layer 331 and the second layer 332 to collapse toward each other because of the vacuum created within the spaces between the closed cells 340. Although apposition forces may cause the closed cells 340 to change shape or flatten somewhat during the application of negative pressure to the tissue interface 108, the volume of the closed cells 340 remains substantially constant and, as a result, maintains fluid flow through the negative-pressure pathway 336 to continue providing negative pressure therapy to the tissue site 150 and measuring the pressure provided by the pressure-sensing pathways 334 and 338. The closed cells 340 also provide a cushion to help prevent the enclosed spaces of the dressing interface 107 from collapsing as a result of external forces as described above. The closed cells 340 disposed in the negative-pressure pathway 336 may be sized and arranged in a pattern that may increase fluid flow of negative pressure being applied to the tissue interface 108 to facilitate the removal of fluids and exudates within the recessed space 344. The closed cells 340 disposed in the pressure-sensing pathways 334 and 338 may be sized and arranged in a pattern to facilitate pressure sensing within the recessed space 344 while impeding the inflow of fluids and exudates into the sensing pathways 334 and 338 to reduce the possibility of blockages.

Figure 8A:
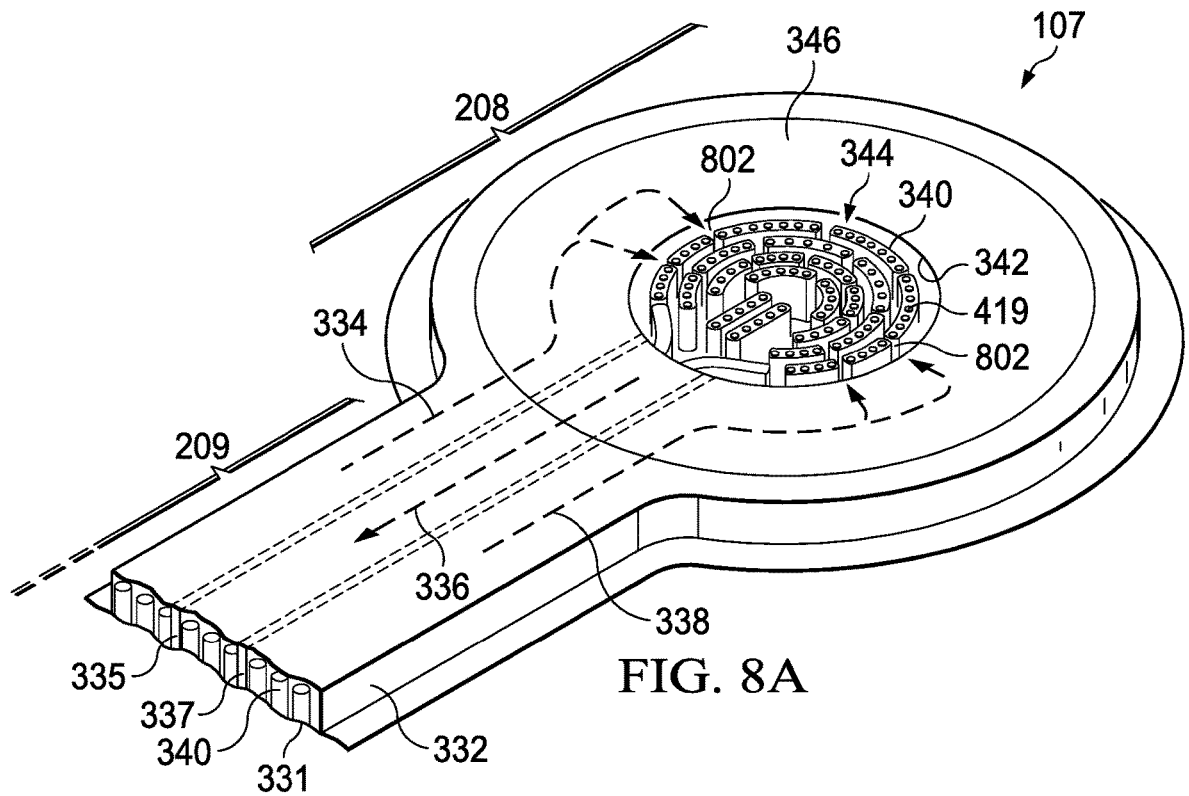
FIG. 8A is a segmented perspective view of an example applicator having a low profile structure that may be associated with some embodiments of the therapy system of FIG. 1.
Figure 8B:
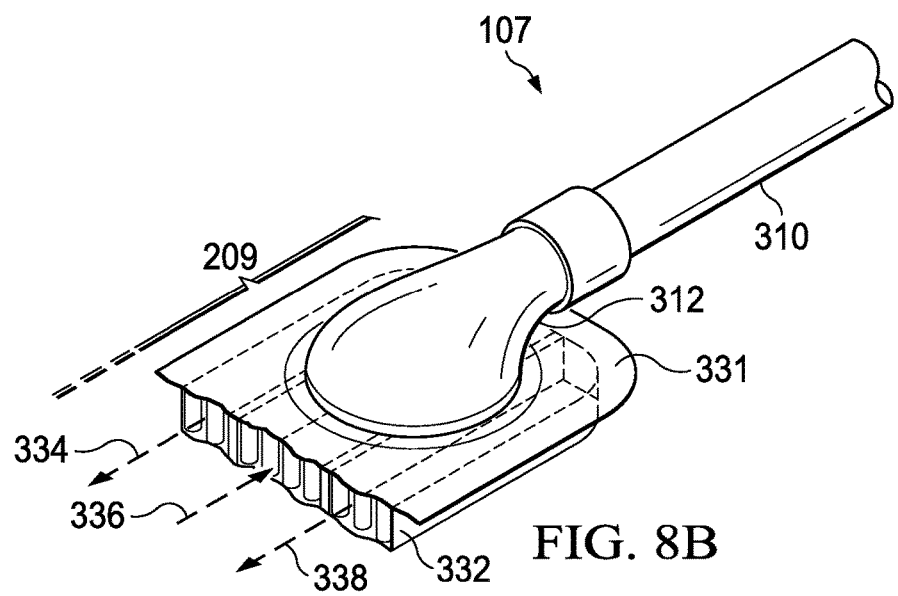
FIG. 8B is a segmented perspective view of an example adapter portion having a low profile structure that may be associated with some example embodiments of the therapy system of FIG. 1.
Figure 9:
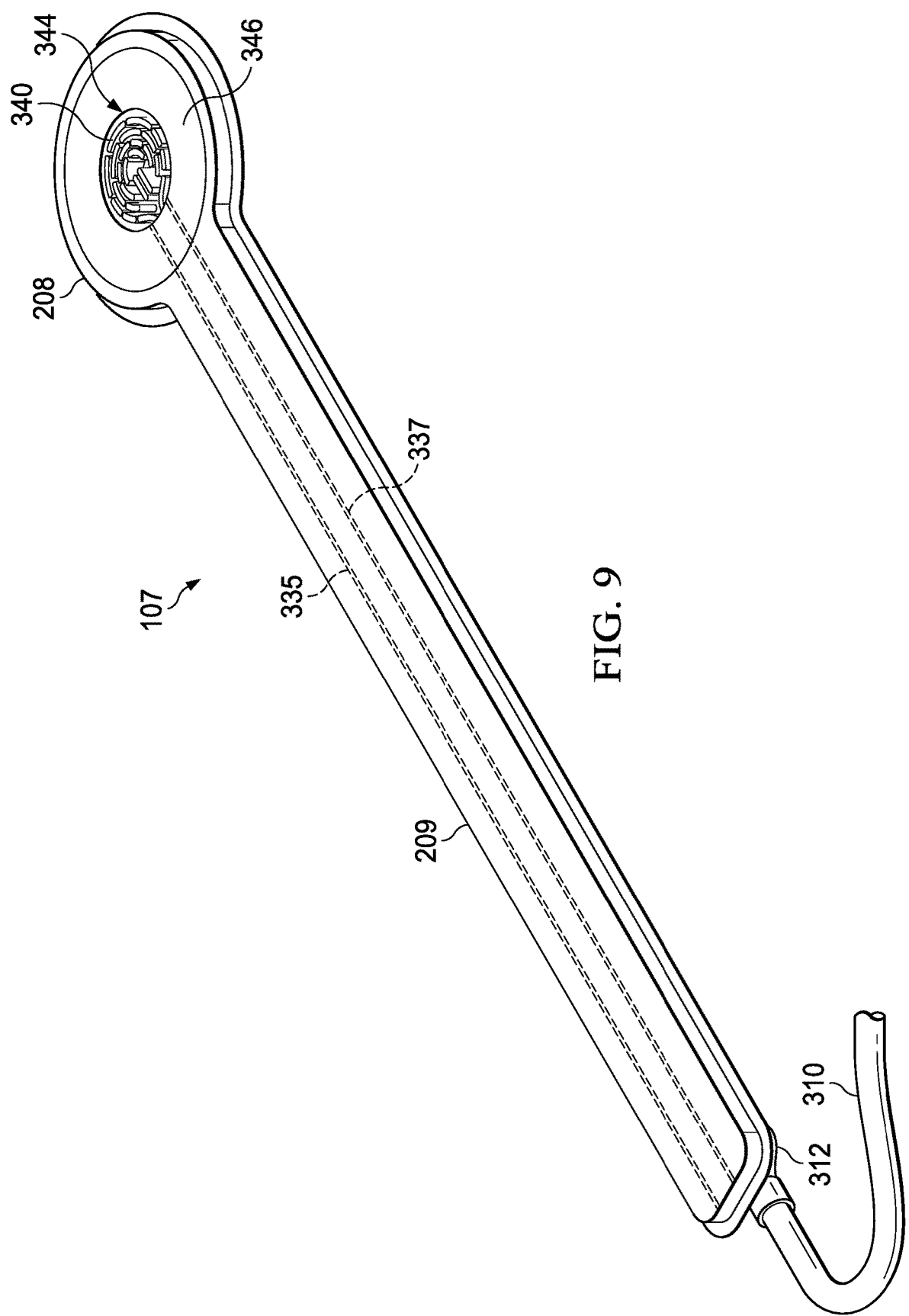
FIG. 9 is a perspective view of another example dressing interface having a low profile structure that may be associated with some example embodiments of the therapy system of FIG. 1.

The closed cells 340 of the dressing interface 107 may have a variety of shapes, and may be sized and arranged in different patterns within the enclosed space to enhance the delivery of negative pressure to the tissue interface 108 for a specific type of tissue site while optimizing pressure sensing and measurement of the negative pressure within the recessed space 344. Another example of the dressing interface 107 is shown in FIGS. 8A, 8B, and 9. FIGS. 8A and 8B are segmented perspective views of the bottom and top of the dressing interface 107 having a low-profile structure that may be associated with some example embodiments of the therapy system of FIG. 1. FIG. 9 is a perspective bottom view of the dressing interface 107 having a low-profile structure that may be associated with some example embodiments of the therapy system of FIG. 1 including both the bottom view shown in FIG. 8A. The applicator 208 of FIG. 8A has a circular shape. The adapter 210 of FIG. 8B may be functionally the same as the adapter 210 of FIG. 3, but has a different structure that may include a semi-rigid elbow connector having a low-profile configuration.

Referring more specifically to FIGS. 8A and 9, the aperture 342 in the second layer 332 may have a generally circular shape that opens to the recessed space 344. Additionally, the closed cells 340 may have a generally elongated and convex shape and may be arranged in a generally circular pattern disposed within the recessed space 344. The closed cells 340 may also comprise surface features, similar to the nodes 419. The closed cells 340 disposed in the center of the recessed space 344 may be more aligned with the negative-pressure pathway 336 to increase fluid flow of negative pressure being applied to the tissue interface 108 to facilitate the removal of fluids and exudates within the recessed space 344. In some embodiments, some of the closed cells 340 may be disposed around the aperture 342 to form a semicircular path opposite the negative-pressure pathway 336 including spaces or gaps 802 between the closed cells 340. The semicircular alignment of the closed cells 340 are positioned within the recessed space 344 to better avoid the flow of fluids passing through from the tissue interface 108 to the negative-pressure pathway 336 when negative pressure is applied. Additionally, the gaps 802 are sufficiently small for further restricting fluid flow into the pressure-sensing pathways 334 and 338 as indicated by the dashed arrows. The gaps 802 facilitate pressure sensing within the recessed space 344 while impeding the inflow of fluids and exudates into the sensing pathways 334 and 338 to reduce the possibility of blockage. In some embodiments, a portion of the aperture perimeter may be welded to the outer circle of the closed cells 340 to further restrict fluid flow to the pressure-sensing pathways 334 and 338 in order to further impede the inflow of fluids and exudates without inhibiting pressure sensing within the recessed space 344.

The closed cells 340 of the dressing interface 107 may have a variety of shapes, and may be sized and arranged in different patterns within the enclosed space to enhance the delivery of negative pressure to the tissue interface 108 for a specific type of tissue site while optimizing pressure sensing and measurement of the negative pressure within the recessed space 344.

Figure 10:
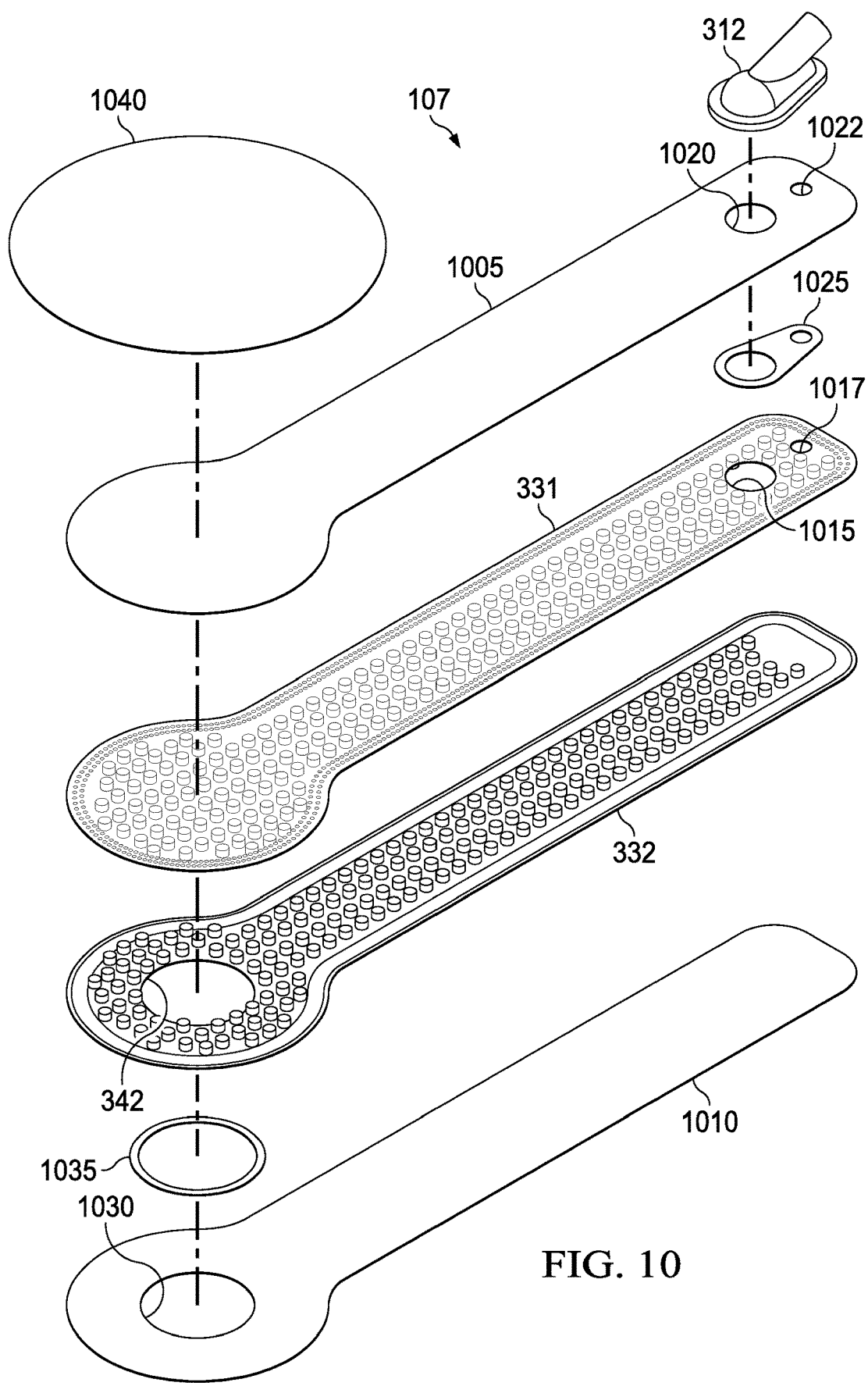
FIG. 10 is an assembly view of another example dressing interface, illustrating additional details of a low profile structure that may be associated with some example embodiments of the therapy system of FIG. 1.

FIG. 10 is a perspective assembly view of another example of the dressing interface 107 having a low-profile structure that may be associated with some example embodiments of the therapy system of FIG. 1. In the example of FIG. 10, the first layer 331 and the second layer 332 of the dressing interface 107 may be covered with a top film coat 1005 and a base film coat 1010, respectively. In some embodiments, the top film coat 1005 and the base film coat 1010 may be sealed around their perimeter by a weld to enclose the space between the first layer 331 and the top film coat 1005 and the space between the second layer 332 and the base film coat 1010. In some embodiments, the perimeter between all the layers may be sealed or attached together along the perimeter.

The blisters 404 of the first layer 331 and the second layer 332 may be positioned in corresponding pairs such that closed ends of the blisters 404 on second layer 332 are positioned opposite closed ends of the blisters 404 in the first layer 331. The blisters 404 in the first layer 331 and the second layer 332 may contact each other at the respective closed ends.

The first layer 331 and the top film coat 1005 may each have ports 1015 and 1020, respectively, through which fluids from the fluid pathways 336 may flow through the adapter 210 to the conduit 310. The first layer 331 and the top film coat 1005 may additionally have ports 1017 and 1022, respectively, which may be fluidly coupled to the conduit 122 through the adapter 210. The dressing interface 107 may further comprise a fluid exit bond 1025 which may be, for example, a weld between the first layer 331 and the top film coat 1005 to seal their respective ports 1015 and 1020 to prevent leakage of fluids flowing through the ports 1015 and 1020. The base film coat 1010 may have a port 1030 concentric with the aperture 342 of the second layer 332. The dressing interface 107 may further comprise a fluid exit bond 1035 which may be, for example, a weld between the second layer 332 and the base film coat 1010 to seal the aperture 342 and the port 1030 to prevent leakage of fluids flowing through them from the tissue interface 108 into the recessed space 344. The other side of the base film coat 1010 may include an attachment device (not shown), such as the attachment device 202. In some embodiments, a top drape 1040 may be utilized to cover the applicator 208 to provide additional protection and support over the applicator 208 if the dressing interface 107 is applied to a tissue site. In some embodiments, the top drape 1040 may also be utilized to cover any adhesive that might be exposed from applying the dressing interface 107 to a tissue site. In some embodiments, the top drape 1040 may be similar to the cover 106. For example, the top drape 1040 may be a polymer such as a polyurethane film.

Figure 11A:
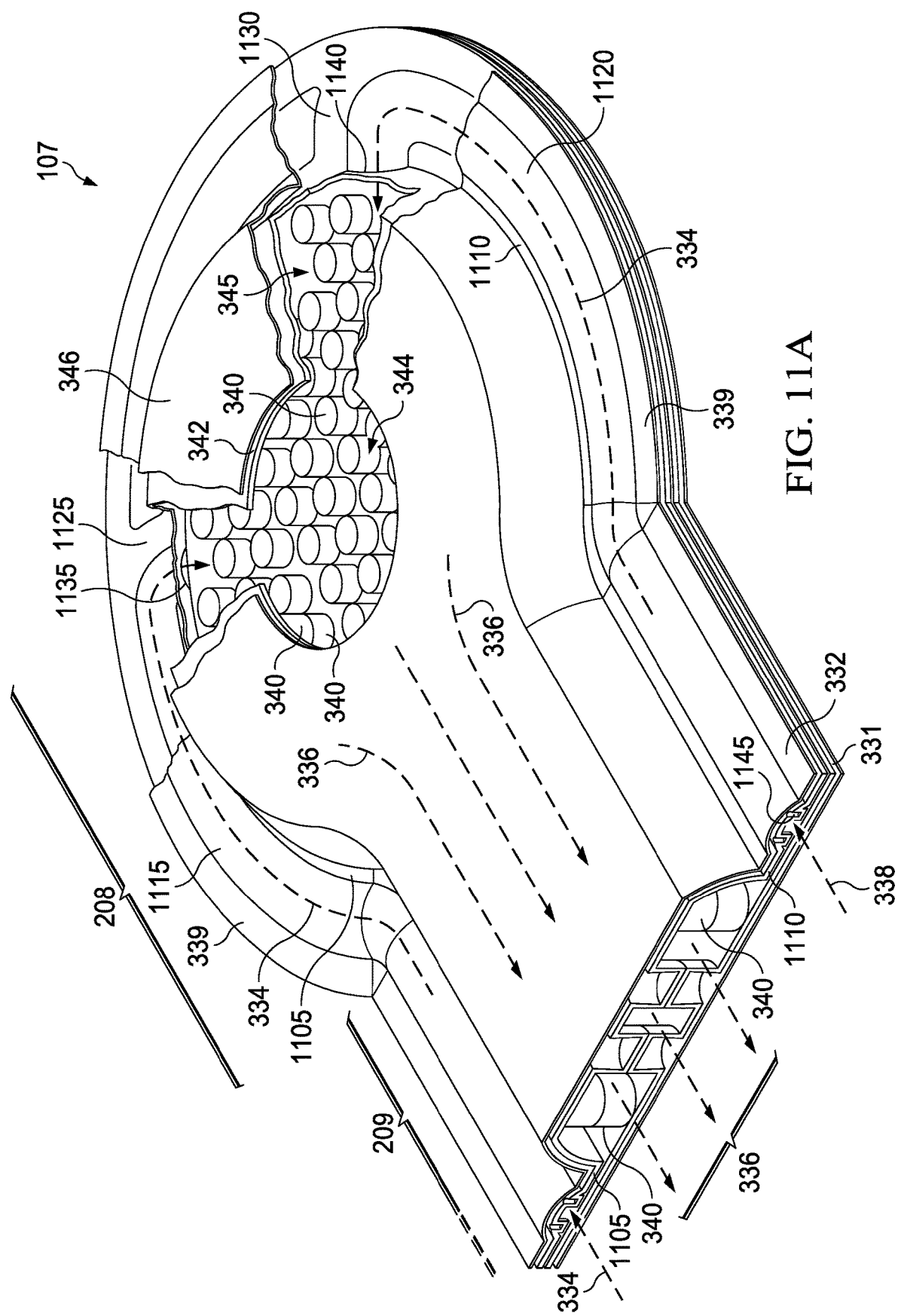
FIG. 11A is a segmented perspective view of an example applicator, illustrating additional details that may be associated with some embodiments of the dressing interface of FIG. 10.
Figure 11B:
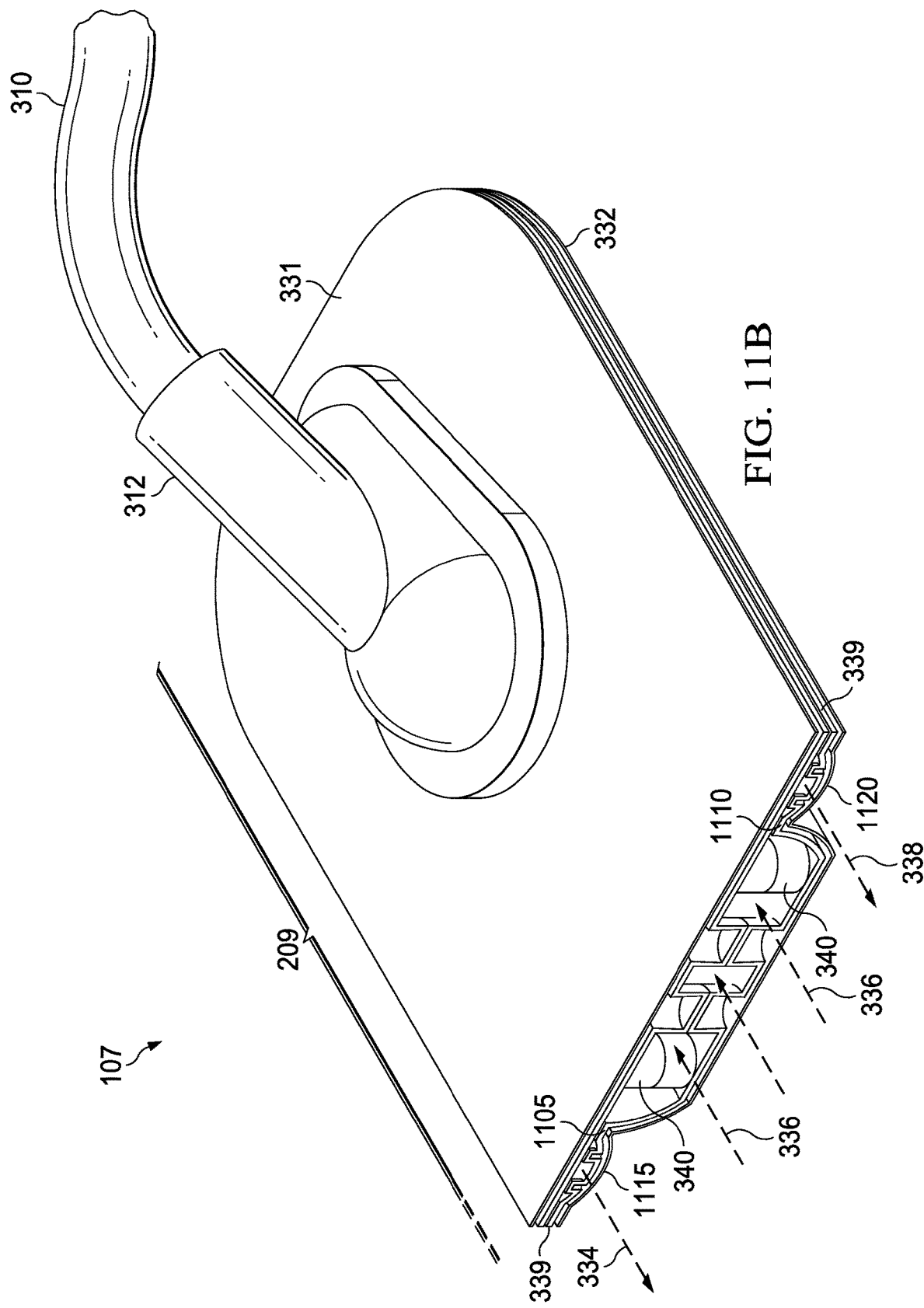
FIG. 11B is a segmented perspective view of an example adapter portion, illustrating additional details that may be associated with some embodiments of the dressing interface of FIG. 10.

FIGS. 11A and 11B are segmented perspective bottom and top views, respectively, of the applicator 208 and the adapter 210 of the dressing interface 107 of FIG. 10. The dressing interface 107 may further comprise at least one barrier or wall such as, for example, a first wall 1105, coupled between the first layer 331 and the second layer 332. In some embodiments, the first wall 1105 may extend from the end of the bridge 209 adjacent the adapter 210 into the applicator 208 to form at least two enclosed spaces or fluid pathways between the first layer 331 and the second layer 332 within the dressing interface 107. In some examples, the dressing interface 107 may further comprise a second barrier such as, for example, a second wall 1110, coupled between the first layer 331 and the second layer 332. In some embodiments, the second wall 1110 also may extend from the end of the bridge 209 adjacent the adapter 210 into the applicator 208. In some example embodiments, the first wall 1105 and the second wall 1110 may comprise a polymeric film coupled between the first layer 331 and the second layer 332. In some other example embodiments, the first wall 1105 and the second wall 1110 may comprise a weld (RF or ultrasonic), a heat seal, an adhesive bond, or a combination of any of the foregoing. In some embodiments comprising two walls, e.g., the first wall 1105 and the second wall 1110, such embodiments may form three enclosed spaces or fluid pathways within the enclosed space between the first layer 331 and the second layer 332. In some embodiments, the first wall 1105 and the second wall 1110 cooperate with the flange 339 to form fluid conductors 1115 and 1120 for two of the fluid pathways that may be dedicated to measuring pressure such as, for example, pressure-sensing pathways 334 and 338 (as indicated by the dashed line arrows), leaving one of the fluid pathways to be utilized for providing negative pressure such as, for example, negative-pressure pathway 336 (as indicated by the dashed line arrows). In some example embodiments, the fluid conductors 1115 and 1120 may have a height having a value in a range between about 0.25 mm and about 3 mm. In some example embodiments, the fluid conductors 1115 and 1120 may have a width having a value in a range between about 1 mm and about 7.5 mm. Thus, the fluid conductors 1115 and 1120 may have a cross-sectional area having a value in a range between about 0.17 mm$^2$ and 16.77 mm$^2$. In some embodiments, the fluid conductors 1115 and 1120 may have a cross-sectional area having a value in a range between about 0.1 mm$^2$ and 18 mm$^2$.

In some example embodiments, the fluid conductors 1115 and 1120 and the fluid pathways 334, 336 and 338 may be fluidly coupled to the conduit 310 by the adapter 210. For example, the negative-pressure pathway 336 may be fluidly coupled to the conduit 128 so that the negative-pressure pathway 336 functions to deliver negative pressure to the tissue interface 108. The pressure-sensing pathways 334 and 338 may be fluidly coupled to the conduit 122 so that the pressure-sensing pathways 334 and 338 function to sense negative pressure at the tissue interface 108. Each of the pressure-sensing pathways 334 and 338 may be fluidly coupled directly to the conduit 122. In other embodiments, both of the sensing pathways 334 and 338 may be fluidly coupled to a single space (not shown) within the adapter 210 that is also fluidly coupled to the conduit 122. In some example embodiments, the other end of the fluid pathways 334, 336 and 338 may terminate within the applicator 208 of the dressing interface 107 for delivering and sensing the negative pressure associated with the tissue interface 108. In the example of FIG. 11A and FIG. 11B, both sensing pathways 334 and 338 are separate from, and side-by-side with, the negative-pressure pathway 336. The side-by-side orientation of the sensing pathways 334 and 338 with the negative-pressure pathway 336 can form a bridge that is generally flatter than a conduit or similar fluid conductor while still being resistant to collapsing under pressure that could block fluid flow through the fluid pathways.

In some examples, each of the first wall 1105 and the second wall 1110 may extend an angular distance around the proximal end of the applicator 208 and cooperate with blocking walls of the flange 339 such as, for example, blocking walls 1125 and 1130, respectively, to form extensions of the fluid conductors 1115 and 1120, respectively, that may be fluidly coupled to the recessed space 344. In the example of FIG. 11A, the pressure-sensing pathways 334 and 338 are in fluid communication with the recessed space 344 through the fluid conductors 1115 and 1120, which may be fluidly coupled to the recessed space 344 by ports such as, for example, through-holes 1135 and 1140, respectively. In some examples, the fluid conductors 1115 and 1120 may include standoffs or closed cells 1145 to form the pressure-sensing pathways 334 and 338. In other embodiments, the fluid conductors 1115 and 1120 may be opened and supported by a thicker base layer, such as the second layer 332. In still other embodiments, the fluid conductors 1115 and 1120 may comprise or be formed by tubes fluidly coupled to the pressure-sensing pathways 334 and 338 in the bridge 209 and the through-holes 1135 and 1140. The negative-pressure pathway 336 may also be in fluid communication with the recessed space 344 and can be adapted to deliver negative pressure to the tissue interface 108 through the recessed space 344, while the pressure-sensing pathways 334 and 338 are adapted to sense the pressure within the sealed environment through the fluid conductors 1115 and 1120.

Each of the walls 1105 and 1110 can extend at least partially around the proximal end of the applicator 208 that form the fluid conductors 1115 and 1120. For example, in some embodiments each of the walls can extend from about 45° to about 315° from the center of the negative-pressure pathway 336 where the negative-pressure pathway 336 is in fluid communication with the recessed space 344. In some embodiments, the angular distance may be different for each of the fluid conductors 1115 and 1120. For example, the angular distance for each of the fluid conductors 1115 and 1120 may be about 60° and 210°, respectively, from the negative-pressure pathway 336. In some example embodiments, the other ends of the fluid conductors 1115 and 1120 that are in fluid communication with the through-holes 1135 and 1140 may be separated from each other by an angular distance of at least 90°, extending around the applicator 208 in a direction away from the negative-pressure pathway 336. The spacing and disposition of the through-holes 1135 and 1140 from each other, and from the negative-pressure pathway 336, can allow the pressure-sensing pathways 334 and 338 to better avoid the flow of fluids passing through from the tissue interface 108 to the negative-pressure pathway 336 when negative pressure is applied. Additionally, the through-holes 1135 and 1140 are sufficiently small for further restricting fluid flow into the fluid conductors 1115 and 1120 and the pressure-sensing pathways 334 and 338, as indicated by the dashed arrows. In some embodiments, the through-holes 1135 and 1140 may have a cross-sectional area having a value in a range between about 0.17 mm$^2$ and 16.77 mm$^2$. In some embodiments, the through-holes 1135 and 1140 may have a cross-sectional area having a value in a range between about 0.1 mm$^2$ and 18 mm$^2$ to further restrict fluid flow to the pressure-sensing pathways 334 and 338 in order to further impede the inflow of fluids and exudates without inhibiting pressure sensing within the recessed space 344.

Figure 12:
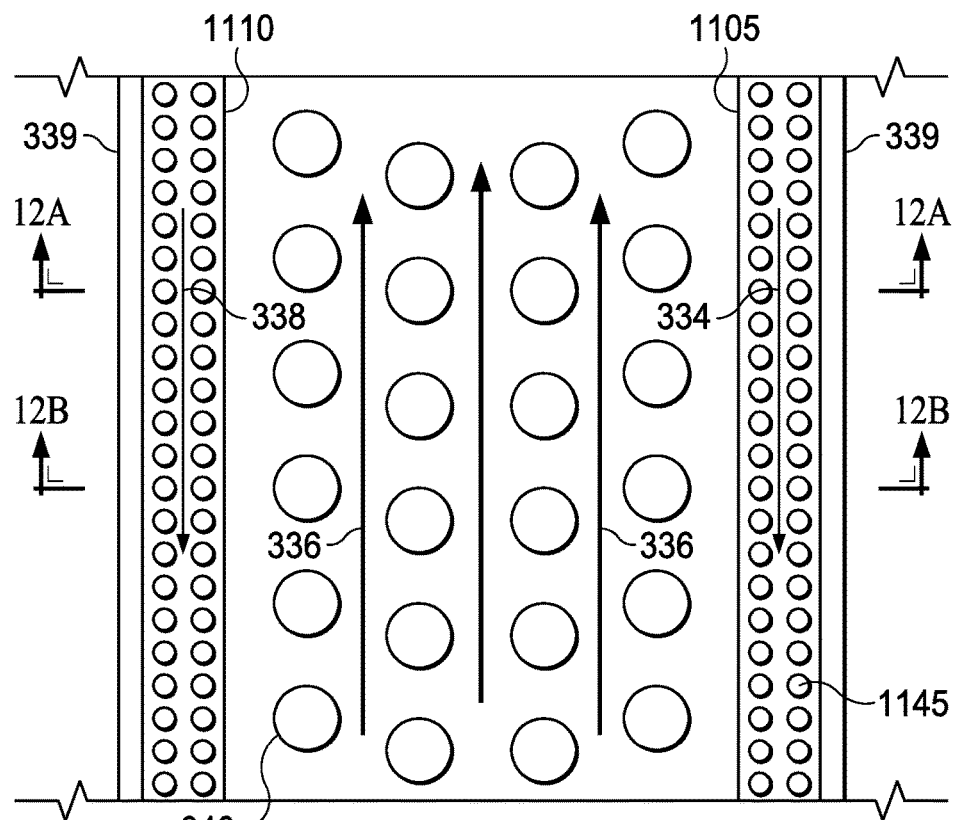
FIG. 12 is a partial top view of a portion of the assembled dressing interface of FIG. 10.
Figure 12A:
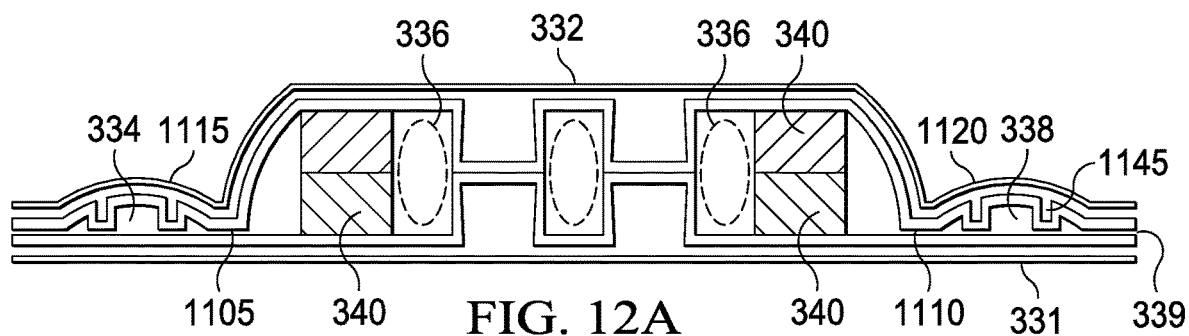
FIGS. 12A and 12B are cross-sectional views taken along lines 12A-12A and 12B-12B in FIG. 12.
Figure 12B:
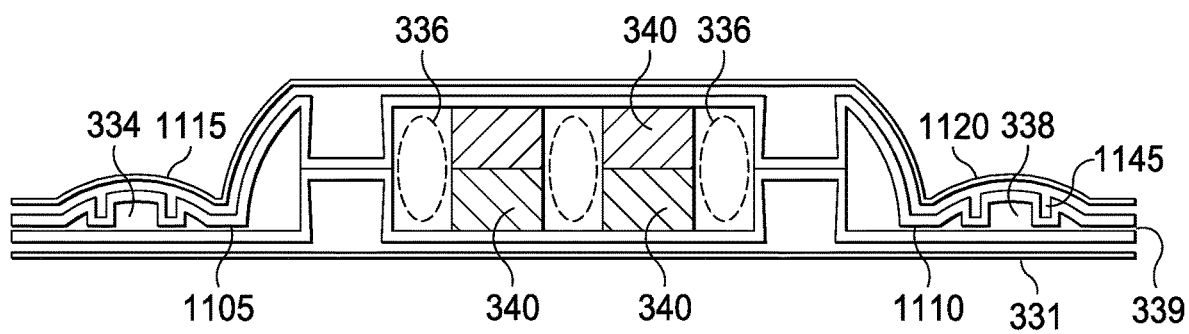

FIG. 12 is a partial top view of the assembled dressing interface 107 of FIG. 10, illustrating additional details that may be associated with some embodiments. FIG. 12A is a section view of the first layer 331 of FIG. 12 taken along line 12A-12A, and FIG. 12B is a section view of the first layer 331 of FIG. 12 taken along line 12B-12B. The closed cells 340 may have a variety of shapes sized and arranged in different patterns within the enclosed space. For example, as illustrated in the examples of FIG. 12A and FIG. 12B, the bridge 209 may comprise two sets of closed cells 340 having a generally cylindrical shape, one set of closed cells 340 extending from the first layer 331 and the other set extending from the second layer 332. In some embodiments, the two sets of closed cells 340 may be opposingly aligned so that the upper portion of the closed cells 340 extending from the first layer 331 face, or are aligned with, the upper portion of the closed cells 340 extending from the second layer 332. The closed cells 340 on the second layer 332 may contact the closed cells on the first layer 331. In some embodiments, the bridge 209 may include four rows of closed cells 340 wherein the closed cells 340 forming the two outside rows are offset or staggered from the closed cells 340 forming the two inside rows as shown. In this particular embodiment, the four rows of closed cells 340 form the negative-pressure pathways 336 as indicated by the three arrows in FIG. 12 and the dashed line ovals shown in FIGS. 12A and 12B. Each of the walls 1105 and 1110 cooperate with the flange 339 to form the two fluid conductors 1115 and 1120. In some embodiments, the fluid conductors 1115 and 1120 may include standoffs or closed cells 1145 to form the pressure-sensing pathways 334 and 338 as shown in FIGS. 12A and 12B.

The closed cells 340 disposed in the negative-pressure pathway 336 may have a larger diameter and pitch than the smaller closed cells 1145 that may increase fluid flow of negative pressure being applied to the tissue interface 108 to facilitate the removal of fluids and exudates within the recessed space 344. The closed cells 1145 disposed in the pressure-sensing pathways 334 and 338 may have a noticeably smaller diameter and pitch than the larger closed cells 340 that may restrict fluid flow to facilitate pressure sensing within the recessed space 344 while impeding the inflow of fluids and exudates into the pressure-sensing pathway 334. The arrangement and dimensions of the closed cells 340 and 1145 may be tailored to manage the delivery of negative pressure to the tissue interface 108 and the measurement of pressure within the recessed space 344.

Figure 13:
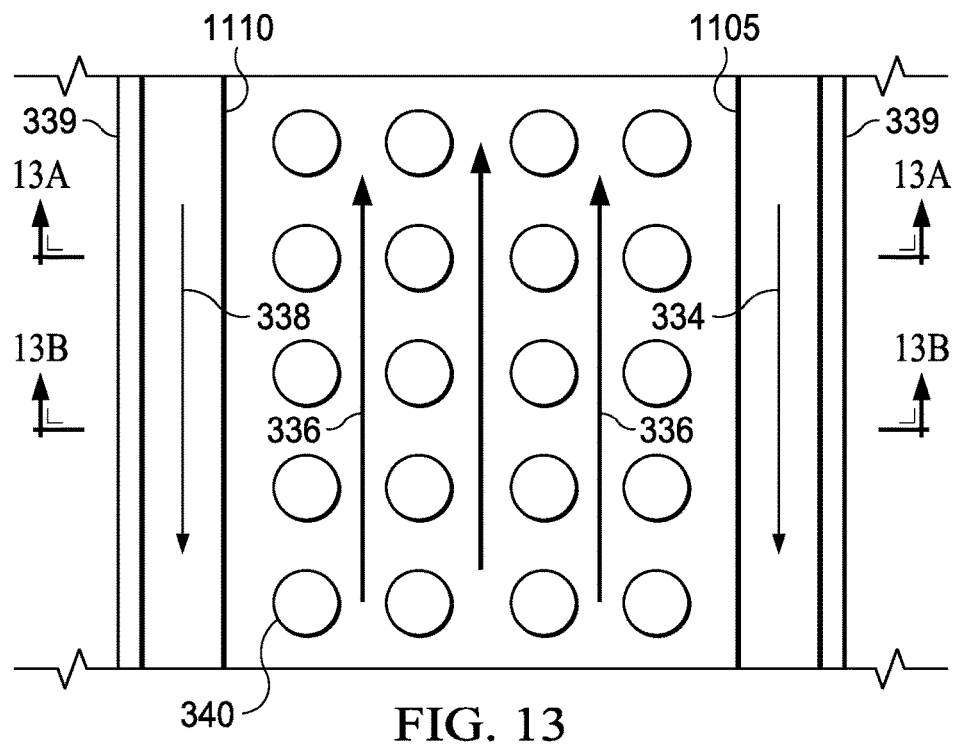
FIG. 13 is a partial top view of a portion of another example of a bridge that may be associated with some embodiments of the dressing interface of FIG. 10.
Figure 13A:
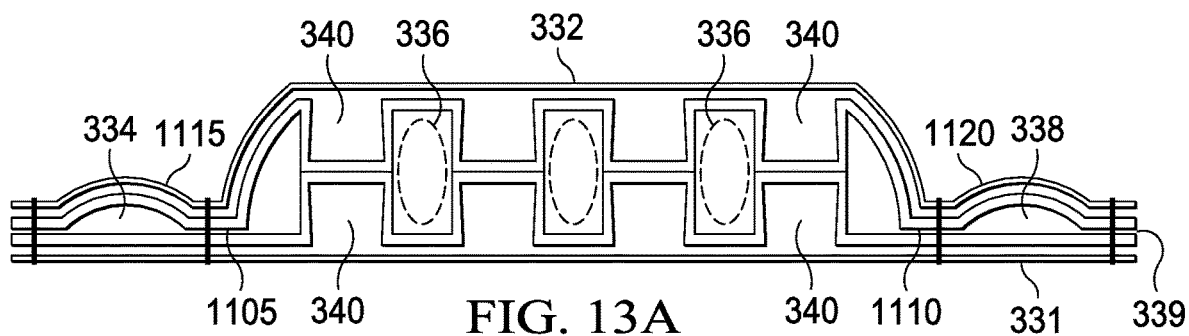
FIGS. 13A and 13B are cross-sectional views taken along lines 13A-13A and 13B-13B in FIG. 13.
Figure 13B:
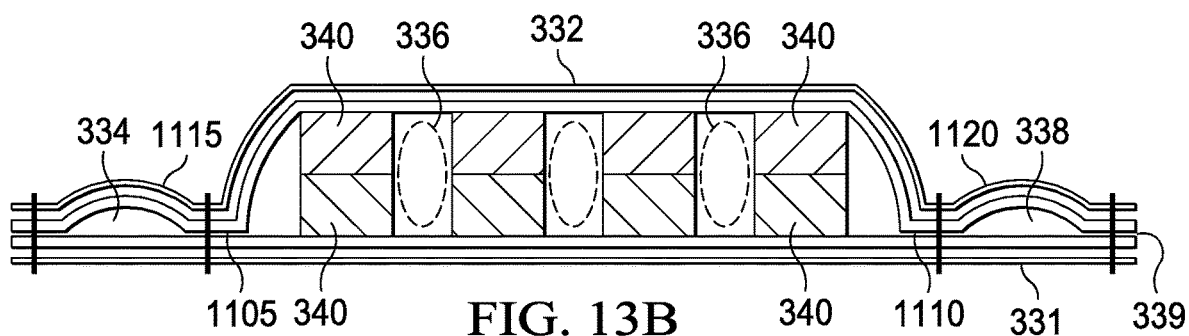

FIG. 13 is a partial top view of another example of the bridge 209. FIGS. 13A, and 13B are cross-sectional views taken along lines 13A-13A, and 13B-13B, in FIG. 13 of the bridge 209. The bridge 209 of FIG. 13 includes four rows of closed cells 340, which are aligned both horizontally and vertically rather than being offset or staggered with each other. In some embodiments, the fluid conductors 1115 and 1120 may be opened and supported by the second layer 332 having an increased thickness. In still other embodiments, the fluid conductors 1115 and 1120 may comprise or be formed by tubes fluidly coupled to the pressure-sensing pathways 334 and 338 in the bridge 209.

The applicator 208 and the bridge 209 may have closed cells with different shapes arranged in different patterns that may be selected as the one best suited for the particular tissue site and the pneumatic requirements of negative-pressure delivery and pressure sensing. For example, the applicator 208 may comprise closed cells that are arranged in a generally circular pattern within the recessed space 344. The closed cells in the enclosed space of the applicator 208 outside the recessed space 344 may also have different shapes arranged in a different pattern to accommodate the sensing pathways 334 and 338.

Figure 14:
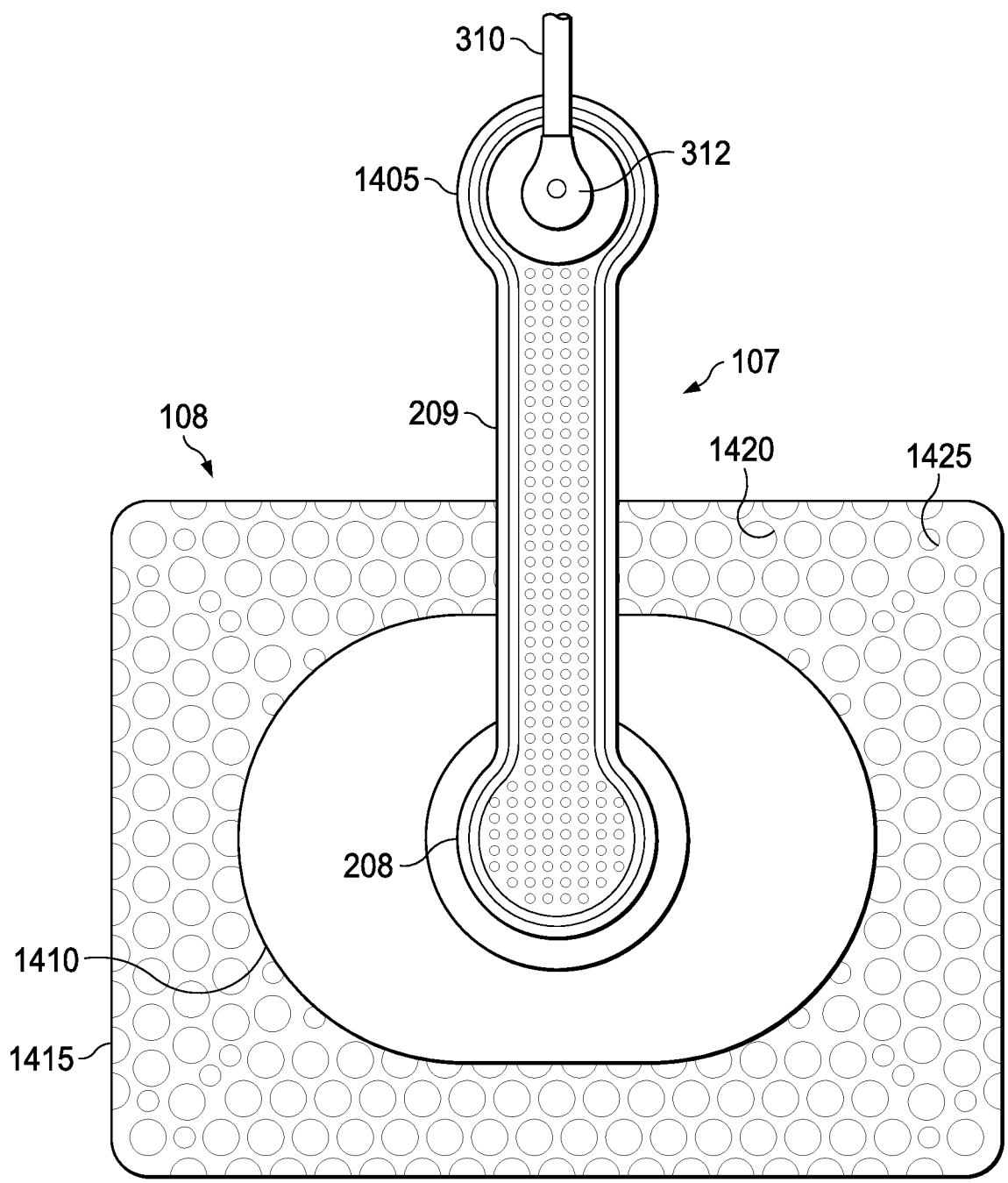
FIG. 14 is a top view of an example of a bridge dressing that may be associated with some embodiments of the therapy system of FIG. 1.

FIG. 14 is a top view of an example of a bridge dressing 1400, illustrating additional details that may be associated with some embodiments of the dressing 102. As illustrated in the example of FIG. 14, the bridge 209 may further comprise a fluid coupler 1405 having a bulbous portion in some embodiments. The fluid coupler 1405 may have a structure substantially similar to the structure of the applicator 208. The fluid coupler 1405 also may comprise a recessed space (not shown) similar to the recessed space 344 that may be in fluid communication with the open space of the adapter 210. For example, the negative-pressure pathway 336 may be fluidly coupled to the conduit 128 through the recessed space of the fluid coupler 1405 and the open space in the adapter 210 so that the negative-pressure pathway 336 receives negative pressure from the negative-pressure source 104 and delivers the negative pressure to the tissue interface 108 through the applicator 208. Correspondingly, pressure-sensing pathways similar to the pressure-sensing pathways 334 and 338 may be fluidly coupled to the conduit 122 so that the pressure-sensing pathways are fluidly coupled to the first sensor 120 and in fluid communication with the recessed space 344 to sense negative pressure at the tissue interface 108. Each of the pressure-sensing pathways may be fluidly coupled directly or indirectly to the conduit 122.

The dressing interface 107 with or without the fluid coupler 1405 may be fluidly coupled to the tissue interface 108, which may comprise a variety of different dressings for negative-pressure therapy. For example, the tissue interface 108 of FIG. 14 may be a composite of dressing layers, including a foam layer 1410, a perforated silicone gel 1415 having apertures 1420 and 1425, a fenestrated polyethylene film (not shown) disposed between the foam layer 1410 and the perforated silicone gel 1415, and an adhesive drape (not shown) covering all three layers. The fenestration pattern of the polyethylene film can be made in registration with the perforation pattern of at least a central area (not shown) of the silicone gel 1415. In some embodiments, each of the perforations in the central area may have a width or diameter of about 2 millimeters, and each of the fenestrations in the polyethylene film may be slots having a length of about 3 millimeters and a width of about 0.5 millimeters to about 1 millimeter. The foam layer 1410 may be foam having an open-cell structure, such as a reticulated foam. The foam may also be relatively thin and hydrophobic to reduce the fluid hold capacity of the dressing, which can encourage exudate and other fluid to pass quickly to external storage. The foam layer may also be thin to reduce the dressing profile and increase flexibility, which can enable it to conform to wound beds and other tissue sites under negative pressure. The adhesive drape may have an aperture or opening adapted to be fluidly coupled to the recessed space 344 of the applicator 208.

The fluid restrictions may comprise a plurality of linear slits or slots in some embodiments. For example, the fluid restrictions may comprise a plurality of linear slots having a length of approximately 4 millimeters or less, and a width of approximately 2 millimeters or less. A length of approximately 3 millimeters and a width of approximately 1 millimeter may be suitable for many therapeutic applications. In some embodiments, the fluid restrictions may be distributed across the polymer film in a uniform pattern, such as a grid of parallel rows and columns. In some embodiments, the fluid restrictions may be distributed across the polymer film in parallel rows and columns, and the rows may be spaced about 3 millimeters apart from each other. The fluid restrictions in each of the rows may also be spaced about 3 millimeters apart from each other in some examples.

Figure 15:
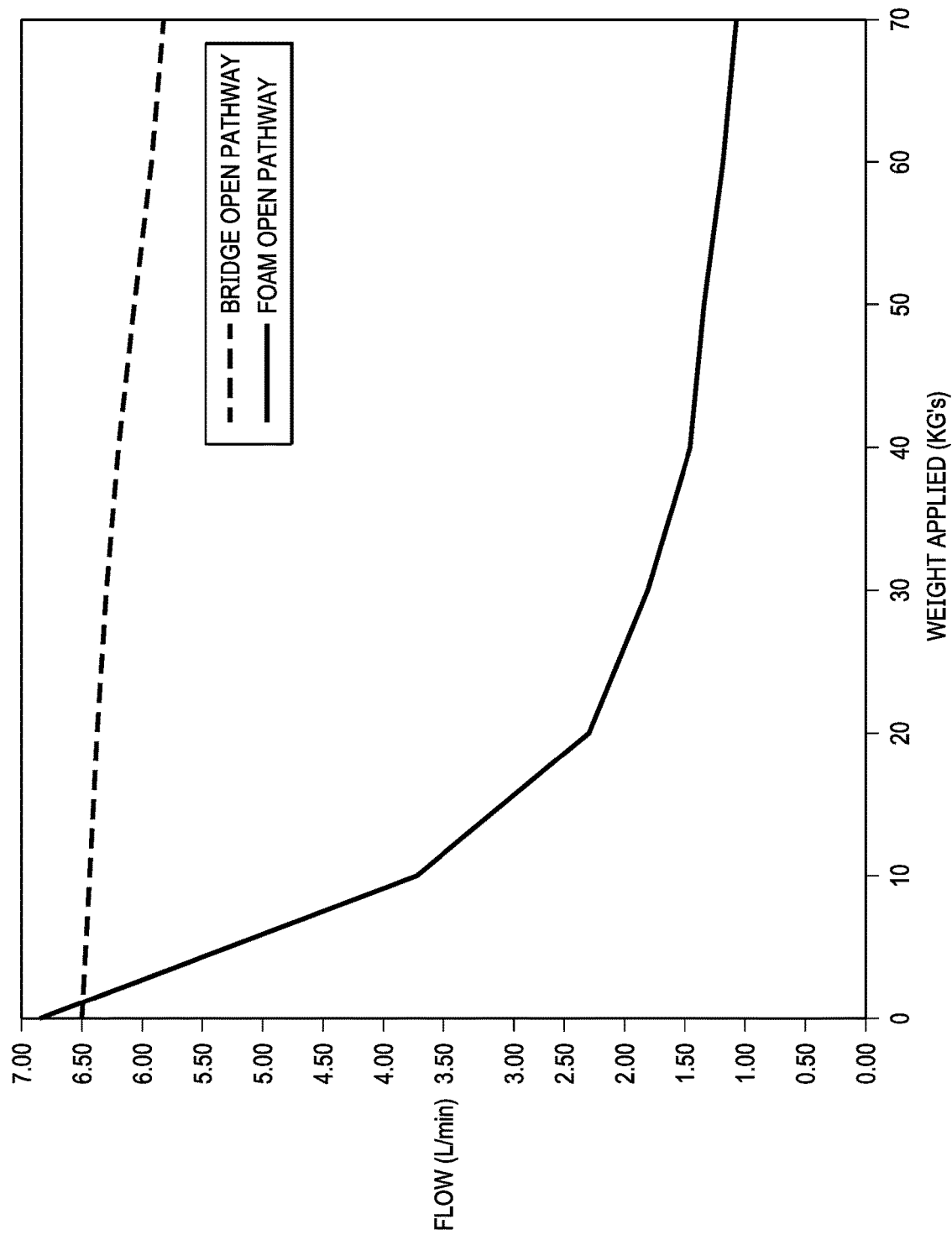
FIG. 15 is a graph illustrating flow rates of fluids drawn through an embodiment of the dressing interface of FIG. 1.

FIG. 15 shows a first graph illustrating flow rates (L/min) of fluids drawn through an embodiment of the bridge 209, as shown by the dashed line, which varies as a result of the application of a flat compressive force to the bridge 209. FIG. 15 shows a second graph illustrating flow rates (L/min) of fluids drawn through a foam conduit fluidly coupled to a standard elbow connector as shown by the solid line that also varies as a result of the application of a flat compressive force to the conduit portion of the elbow connector. In each case, 25 mmHg of negative pressure was applied by both the dressing interface 107 and the elbow connector to a foam pad with 1.0 mpas of fluid. Both devices were subjected to these compressive forces over a range of 0-70 kg. Fluid flow for the bridge 209 suffered a loss in fluid flow of only 10% at 70 kg, while the foam conduit suffered a loss of about 85% at 70 kg. Fundamentally, the flow rate through the bridge 209 exceeded the flow rate of the foam conduit over the entire range of 0-70 kg and, as such, is less susceptible to blockages. Thus, the performance of the bridge 209 exceeded the performance of the foam conduit with the application of flat a compressive force.

Figure 16:
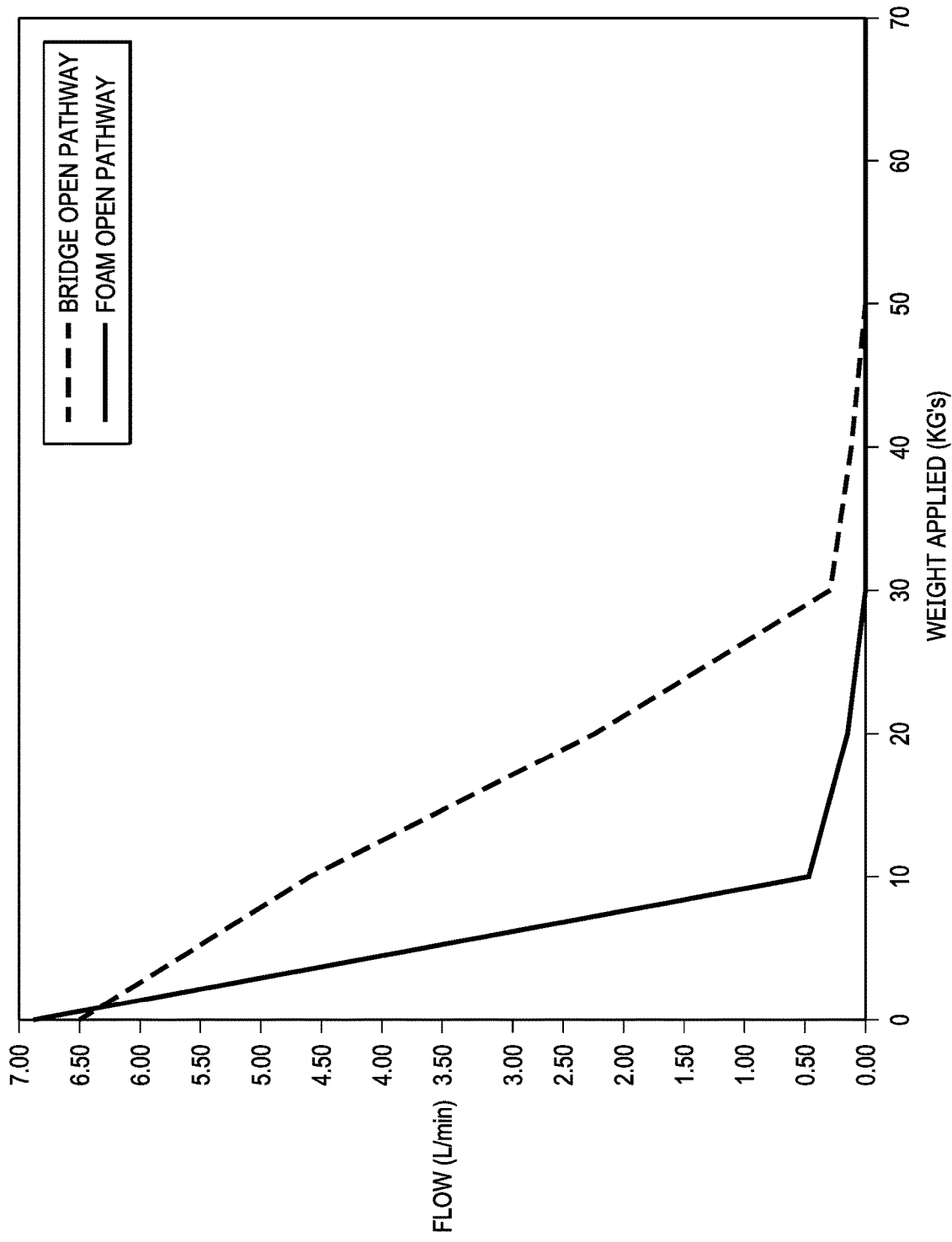
FIG. 16 is a graph illustrating flow rates of fluids drawn through an embodiment of the dressing interface of FIG. 1.

FIG. 16 shows a first graph illustrating flow rates (L/min) of fluids drawn through an example of the bridge 209, as shown by the dashed line, which varies as a result of the application of a compressive force on a horizontal point of the bridge 209, as opposed to a flat compressive force. FIG. 16 also shows a second graph illustrating flow rates (L/min) of fluids drawn through a foam conduit fluidly coupled to a standard elbow connector as shown by the solid line that also varies as a result of the application of a compressive force on a horizontal point of the conduit portion of the elbow connector. In each case, 25 mmHg of negative pressure was applied by both the dressing interface 107 and the elbow connector to a foam pad with 1.0 mpas of fluid. Both devices were subjected to these compressive forces over a range of 0-70 kg. The bridge 209 was able to maintain open flow when subjected to a compressive load of more than 10 to 20 kg greater than was subjected to the foam conduit. Thus, the performance of the bridge 209 exceeded the performance of the foam conduit with the application of a compressive force at a specific horizontal point.

Figure 17:
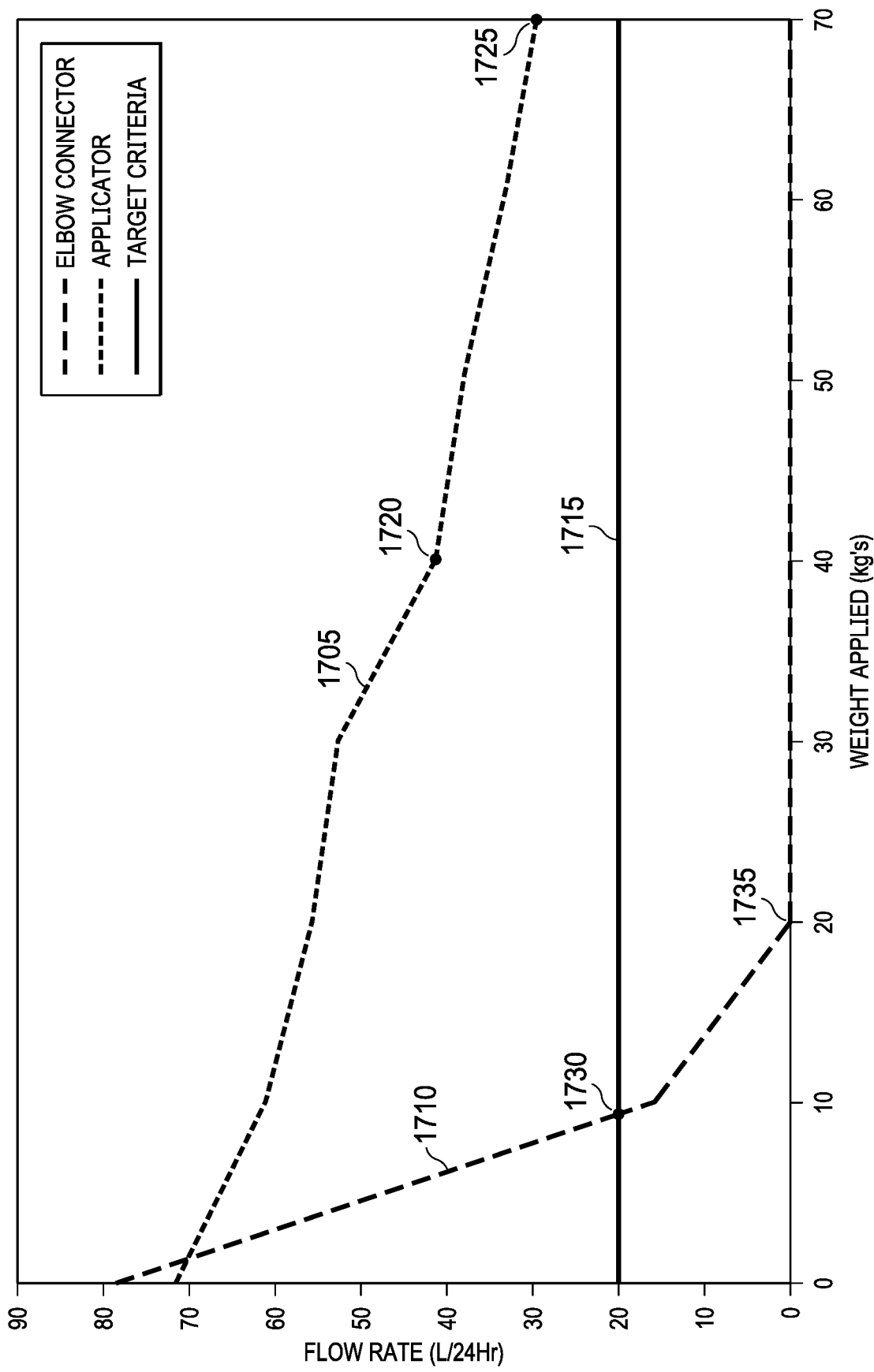
FIG. 17 is a graph illustrating flow rates of fluids drawn through an embodiment of the dressing interface of FIG. 1.

FIG. 17 shows a first graph illustrating flow rates (L/24 Hrs) of fluids drawn through an example of the dressing interface 107, as shown by the dashed line 1705, which vary as a result of the application of a compressive force to an example of the applicator 208. FIG. 17 also shows a second graph illustrating flow rates (L/24 Hrs) of fluids drawn through a standard elbow connector and a conduit fluidly coupled to the connector as shown by the dashed line 1710, which also vary as a result of the application of a compressive force to the elbow connector. In each case, 25 mmHg of negative pressure was applied by both the dressing interface 107 and the elbow connector to a foam pad with 1.0 mpas of fluid. The results for both devices were compared to a target criteria as shown by the solid line 1715 that was set at a minimum value of 20 L/24 hrs over range of 0-70 kg for this type of tissue interface. Fluid flow for the dressing interface 107 was more than twice (100% above) the target criteria with the application of a compressive force of about 40 kg at 1720, and still more than 33% above the target criteria at a maximum compressive force of 70 kg at 1725. The flow rate through the applicator 208 exceeds the minimum flow rate of 20 L/24 hrs over the entire range of 0-70 kg. In comparison, fluid flow for the standard elbow connector fell below the target criteria with the application of a compressive force of only 10 kg at 1730, and fell to a zero flow rate or total blockage at a compression force of 20 kg at 1735. The flow rate through the elbow connector not only did not exceed the minimum flow rate through the entire range of 0-70 kg, but also dropped quickly below the minimum flow rate at only 10 kg. Thus, the performance of the applicator 208 exceeded the performance of the elbow portion of the elbow connector with the application of a compressive force.

Figure 18:
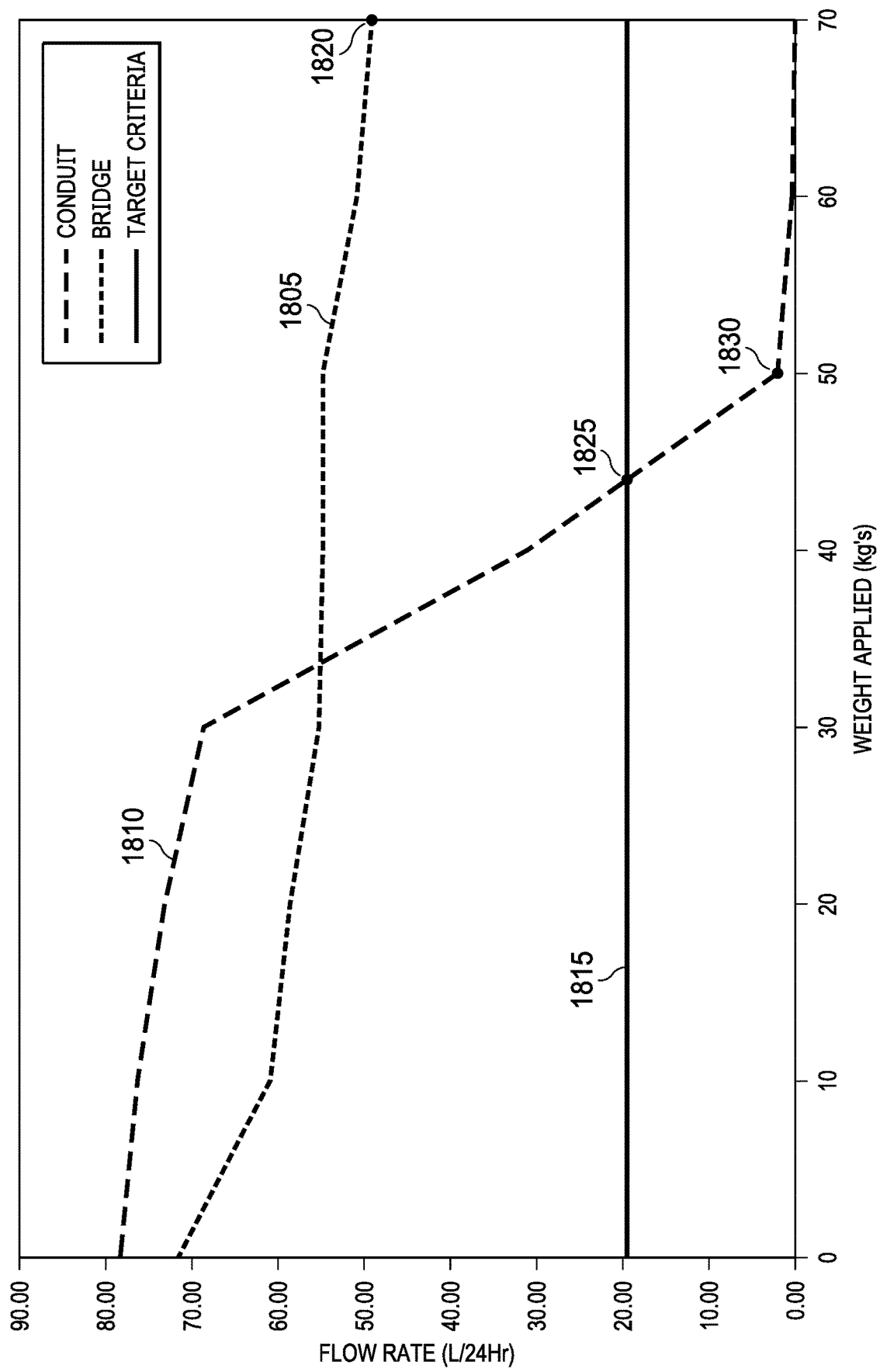
FIG. 18 is a graph illustrating the flow rates of fluids drawn through an embodiment of the dressing interface of FIG. 1.

FIG. 18 shows a first graph illustrating flow rates (L/24 Hrs) of fluids drawn through an example of the dressing interface 107, as shown by the dashed line 1805, which varies as a result of the application of a compressive force to an example of the bridge 209. FIG. 18 also shows a second graph illustrating flow rates (L/24 Hrs) of fluids drawn through a standard elbow connector and a conduit fluidly coupled to the connector as shown by the dashed line 1810 that also varies as a result of the application of a compressive force to the conduit portion of the elbow connector. In each case, 25 mmHg of negative pressure was applied by both the dressing interface 107 and the elbow connector to a foam pad with 1.0 mpas of fluid. The results for both devices were compared to the target criteria as shown by the solid line 1815 that again was set at a minimum value of 20 L/24 hrs over range of 0-70 kg for this type of tissue interface. Fluid flow for the dressing interface 107 was about 150% above the target criteria with the application of a compressive force above the target criteria at a maximum compressive force of 70 kg at 1820 on the bridge 209. The flow rate through the bridge 209 exceeds the minimum flow rate of 20 L/24 hrs over the entire range of 0-70 kg. In comparison, fluid flow for the standard elbow connector fell below the target criteria with the application of a compressive force on the conduit portion of the elbow connector of only 45 kg at 1825, and fell to a nearly zero flow rate or total blockage at a compression force of 50 kg at 1830. The flow rate through the elbow connector not only did not exceed the minimum flow rate through the entire range of 0-70 kg, but also dropped quickly below the minimum flow rate at 45 kg. Thus, the performance of the bridge 209 exceeded the performance of the conduit portion of the elbow connector with the application of a compressive force.

Figure 19:
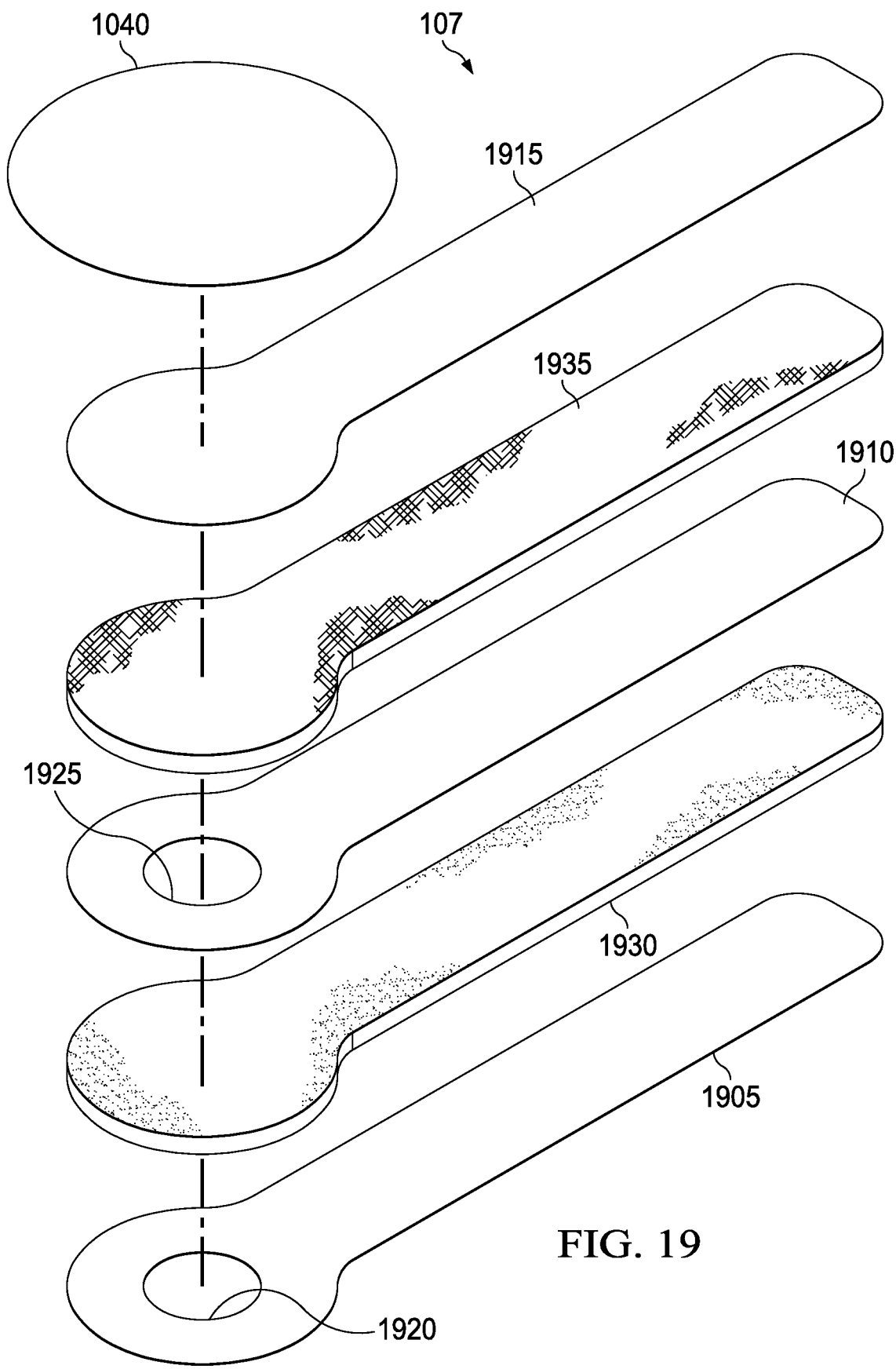
FIG. 19 is an assembly view of another example of a dressing interface, illustrating additional details that may be associated with some embodiments.

FIG. 19 is a perspective assembly view of another example of the dressing interface 107, illustrating additional details that may be associated with some embodiments. In the example of FIG. 19, the dressing interface 107 comprises a first layer 1905, a second layer 1910, and a third layer 1915. In some examples, each of the first layer 1905, the second layer 1910, and the third layer 1915 may comprise or consist of materials similar to the cover 106. For example, each may comprise or consist essentially of a flexible polymer film, such as a polyurethane or polyethylene film. The first layer 1905, the second layer 1910, and the third layer 1915 need not all comprise or consist of the same material. In some examples, the first layer 1905, the second layer 1910, and the third layer 1915 may each have a thickness in a range of about 20 microns to about 50 microns, and may be transparent or light-occlusive. If not transparent, they may have a range of colors, including white. Different layers may be different colors or, alternatively, transparent to improve visibility of contents in the dressing interface 107.

The first layer 1905, the second layer 1910, and the third layer 1915 may each be elongated, having a length substantially greater than width, as illustrated in the example of FIG. 19. In some embodiments, one or more of the first layer 1905, the second layer 1910, and the third layer 1915 may also have a flange at one end, as further illustrated in the example of FIG. 19. As illustrated in the example of FIG. 19, the flange may be circular in some embodiments. The size of the flange may vary. For example, the flange may have a diameter about the same size as the width of the first layer 1905, or may be substantially larger to increase the structural integrity of the dressing interface 107 without a release or support liner.

The first layer 1905 may have a first aperture 1920 disposed near a distal end, and the second layer 1910 may have a second aperture 1925 disposed near a distal end. The first aperture 1920 and the second aperture 1925 may be vertically aligned in some examples, as illustrated in the example of FIG. 19. In some embodiments, the first aperture 1920, the second aperture 1925, or both may be disposed in a flange area.

An attachment device, such as adhesive layer (not shown), may be placed on an outside surface of the distal end of the first layer 1905 in some embodiments. For example, an acrylic or polyurethane adhesive may be disposed around the first aperture 1920 on an outside surface of the flange area. The thickness of the adhesive may vary in different configurations. For example, a support liner may not be necessary with a thicker adhesive, and a thicker adhesive may also increase application ease-of-use. In some examples, the adhesive may have a weight of about 100 grams per square meter to about 200 grams per square meter. Additionally or alternatively, the adhesive may be a light-switchable adhesive.

A first manifold 1930 may be disposed between the first layer 1905 and the second layer 1910. The first manifold 1930 is illustrative of a variety of materials and configurations that are open to pressure and fluid flow, particularly in the form of air and exudate of varying viscosity. In some examples, the first manifold 1930 may be hydrophobic to discourage collection and clotting of exudate, and should resist blocking under compression. Additionally or alternatively, anti-clotting agents may be bound to the first manifold 1930. Examples of materials suitable for some embodiments of the first manifold 1930 may include reticulated foam (preferably having a thickness in a range of about 3 millimeters to about 8 millimeters), combinations of foam and fabric (such as various textiles manufactured by Milliken & Company), or coated or treated foam (such as plasma treated). Additionally or alternatively, the first manifold 1930 may comprise or consist essentially of a low-profile 3D polyester textile, such as textiles manufactured by Baltex.

A second manifold 1935 may be disposed between the second layer 1910 and the third layer 1915. The second manifold 1935 is illustrative of a variety of materials and configurations that are open to pressure and fluid flow, particularly in the form of air. In some examples, the second manifold 1935 may be hydrophobic to discourage ingress of exudate, and should resist blocking under compression. In some embodiments, the second manifold 1935 may be more hydrophobic than the first manifold 1930. Additionally or alternatively, the second manifold 1935 may have a lower stiffness modulus than the first manifold 1930. Examples of materials suitable for some embodiments of the second manifold 1935 may include reticulated foam (preferably having a thickness in a range of about 3 millimeters to about 5 millimeters), felted and compressed reticulated foam (preferably having a thickness in a range of about 2 millimeters to about 4 millimeters), combinations of foam and textiles (such as various textiles manufactured by Milliken & Company), or coated or treated foam (such as plasma treated). Additionally or alternatively, the second manifold 1935 may comprise or consist essentially of a low-profile 3D polyester textile, such as textiles manufactured by Baltex.

Figure 20:
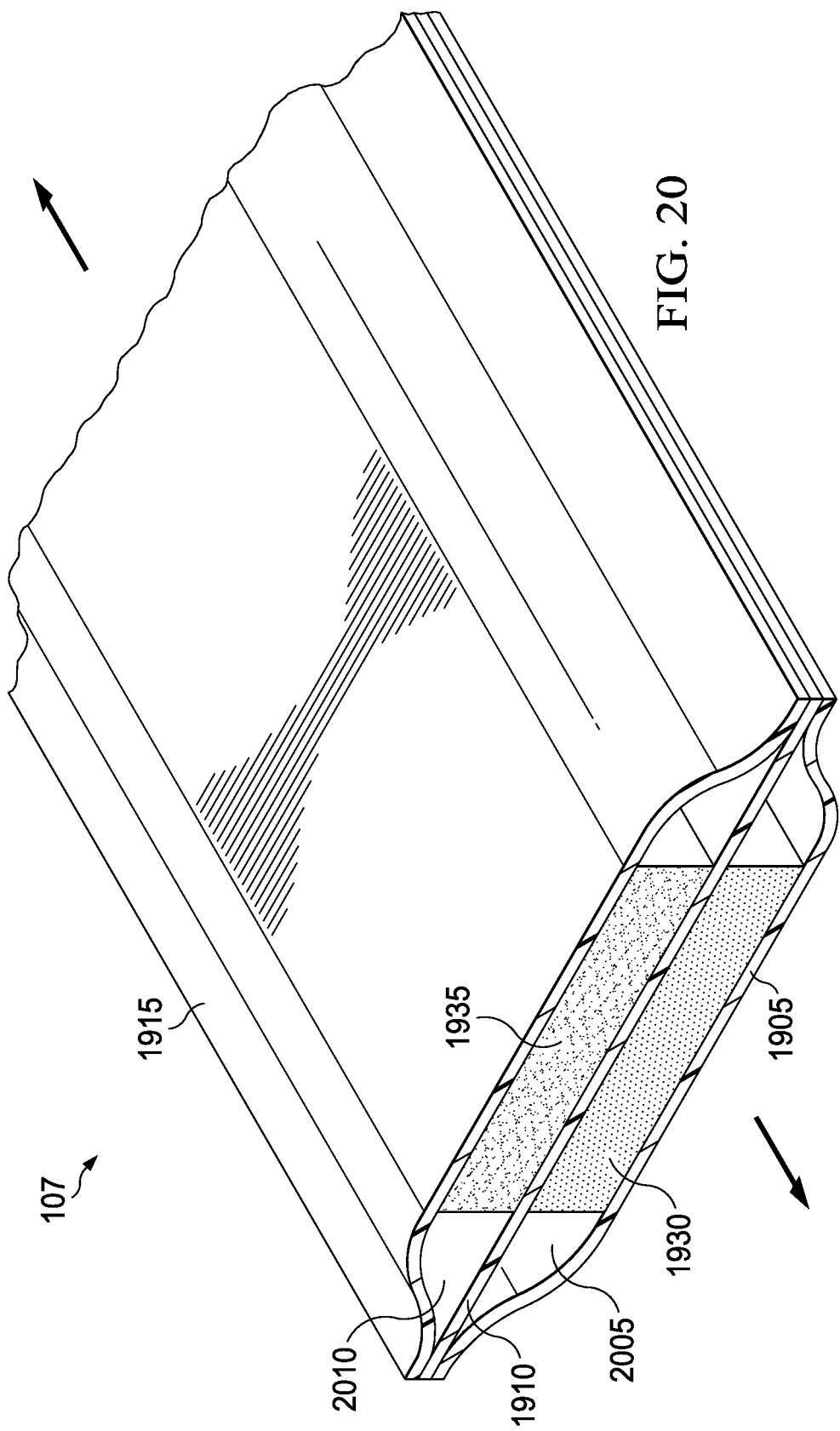
FIG. 20 is an assembled section view of the dressing interface of FIG. 19, illustrating additional details that may be associated with some embodiments.

FIG. 20 is an assembled section view of the dressing interface 107 of FIG. 19, illustrating additional details that may be associated with some embodiments. For example, the first layer 1905, the second layer 1910, and the third layer 1915 may be welded or bonded together to form two longitudinal chambers that run the length of the dressing interface 107. In the example of FIG. 20, edges of the first layer 1905 and the third layer 1915 are sealed to edges of the second layer 1910 to form a first fluid path 2005 and a second fluid path 2010 in a stacked relationship. The second layer 1910 is disposed between and fluidly separates the first fluid path 2005 and the second fluid path 2010. The first manifold 1930 is configured to support the first fluid path 2005, separating a central portion of the first layer 1905 and the second layer 1910. The second manifold 1935 is configured to support the second fluid path 2010, separating the second layer 1910 and the third layer 1915.

In other examples, a fourth layer (not shown) may be integrated to form a third chamber configured to deliver instillation solution. The fourth layer may be comprised of a material similar to either of the first layer 1905, the second layer 1910, or the third layer 1915, for example. In some embodiments, the third chamber may have a volume that is less than the volume of the first fluid path 2005, and may be less than half the volume of the first fluid path 2005 in some examples.

Alternatively, in some embodiments of the dressing interface 107, the first fluid path 2005 and the second fluid path 2010 may be disposed side-by-side instead of in a stacked relationship. A side-by-side configuration may be assembled with only two film layers in some examples.

Figure 21:
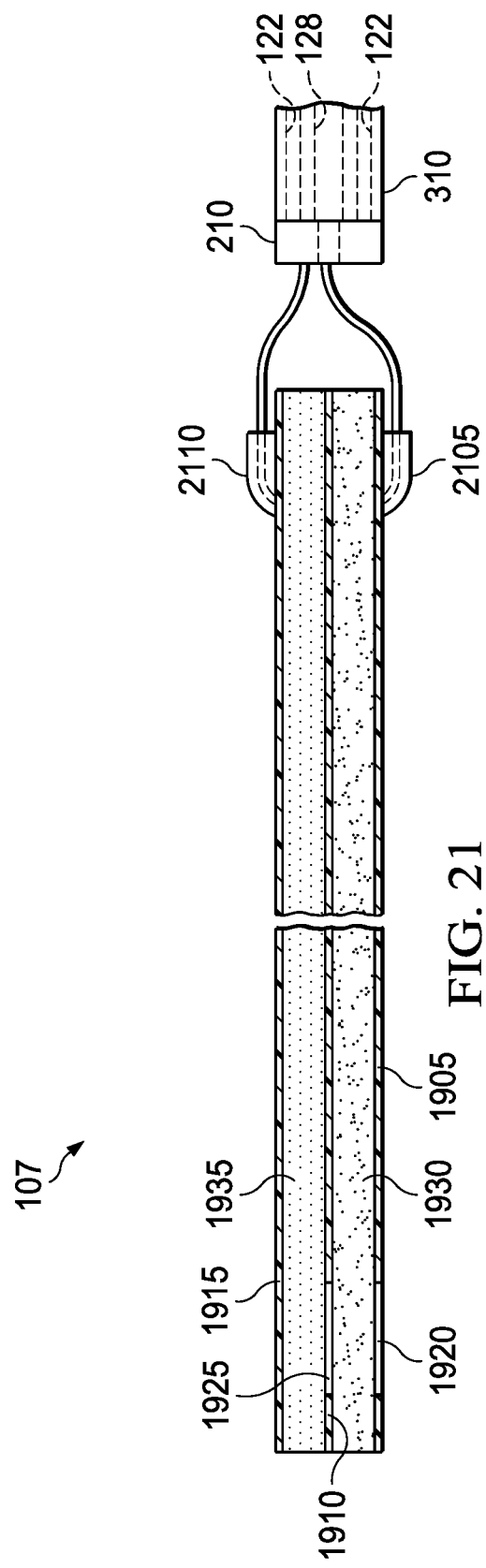
FIG. 21 is a schematic section view of the dressing interface of FIG. 19, illustrating additional details that may be associated with some embodiments.

FIG. 21 is a schematic section view of opposite ends of the dressing interface 107 of FIG. 19, illustrating additional details that may be associated with some embodiments. As illustrated in FIG. 21, the dressing interface 107 may comprise a first port 2105 fluidly coupled to a proximal end of the first fluid path 2005 and a second port 2110 fluidly coupled to a proximal end of the second fluid path 2010. The first fluid path 2005 may be pneumatically isolated from the second fluid path 2010, except through the second aperture 1925.

In use, the first port 2105 and the second port 2110 may be fluidly coupled to the conduit 122 and the conduit 128, and the first aperture 1920 may be oriented to face the dressing 102 or a tissue site to provide a means for pressure and fluid to be communicated to and from a tissue site. As illustrated in the example of FIG. 21, the conduit 122 and the conduit 128 may be combined in the conduit 310, which may include the adapter 210. For example, the first port 2105 may be fluidly coupled to the conduit 128 and the second port 2110 may be fluidly coupled to the conduit 122 through the adapter 210.

Figure 22:
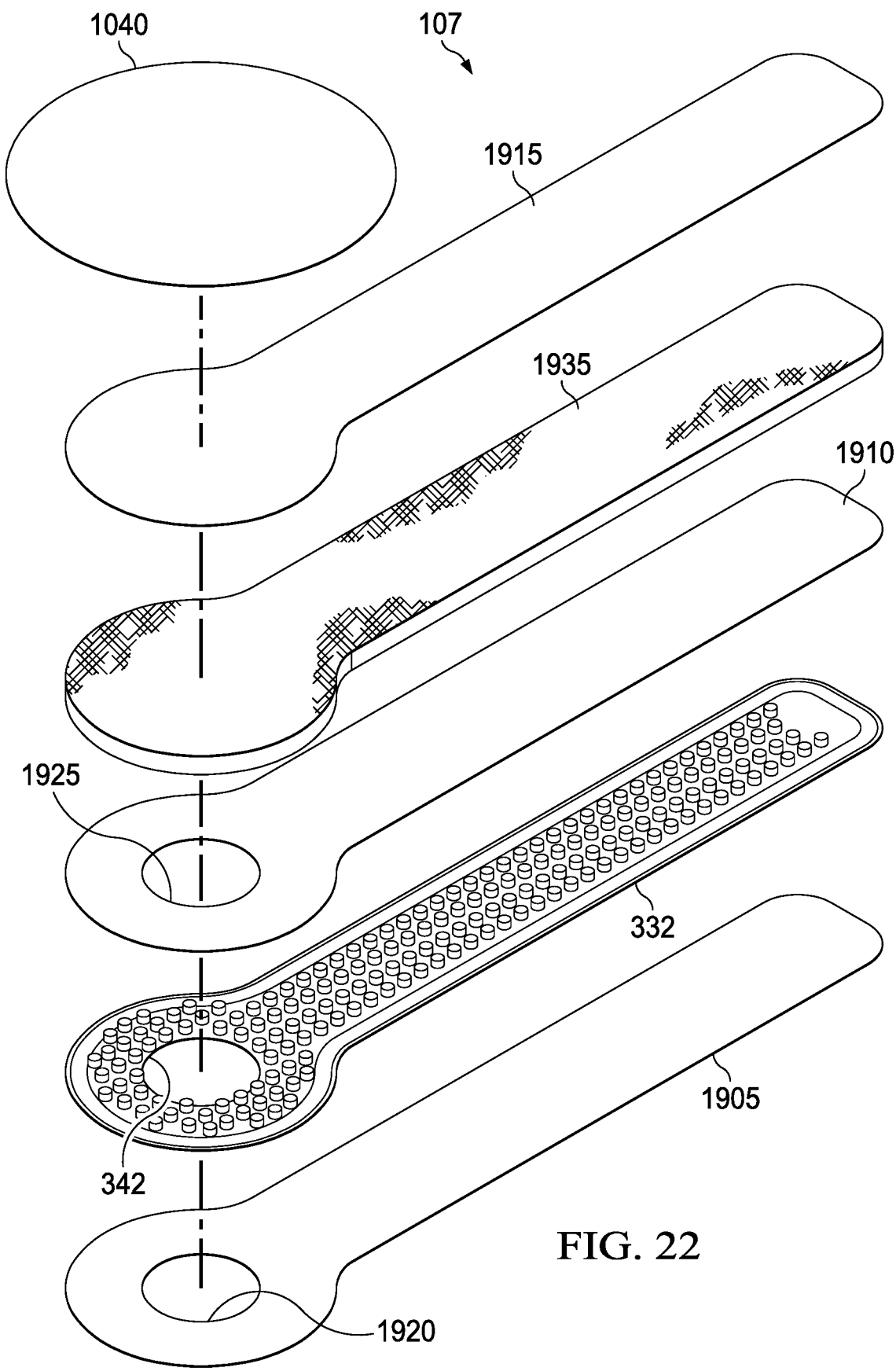
FIG. 22 is an assembly view of another example of a dressing interface, illustrating additional details that may be associated with some embodiments.

In some examples, one or more of the first manifold 1930 and the second manifold 1935 may additionally or alternatively comprise or consist essentially of a layer substantially similar to the first layer 331, the second layer 332, or both, and may have features substantially similar to the closed cells 340, the closed cells 350, or both. FIG. 22, for example, illustrates an embodiment of the dressing interface 107 in which the first manifold 1930 is replaced by the second layer 332 of FIG. 10. The first manifold 1930, the second manifold 1935, or both may have open cells or raised blisters instead of or in addition to closed cells.

Figure 23:
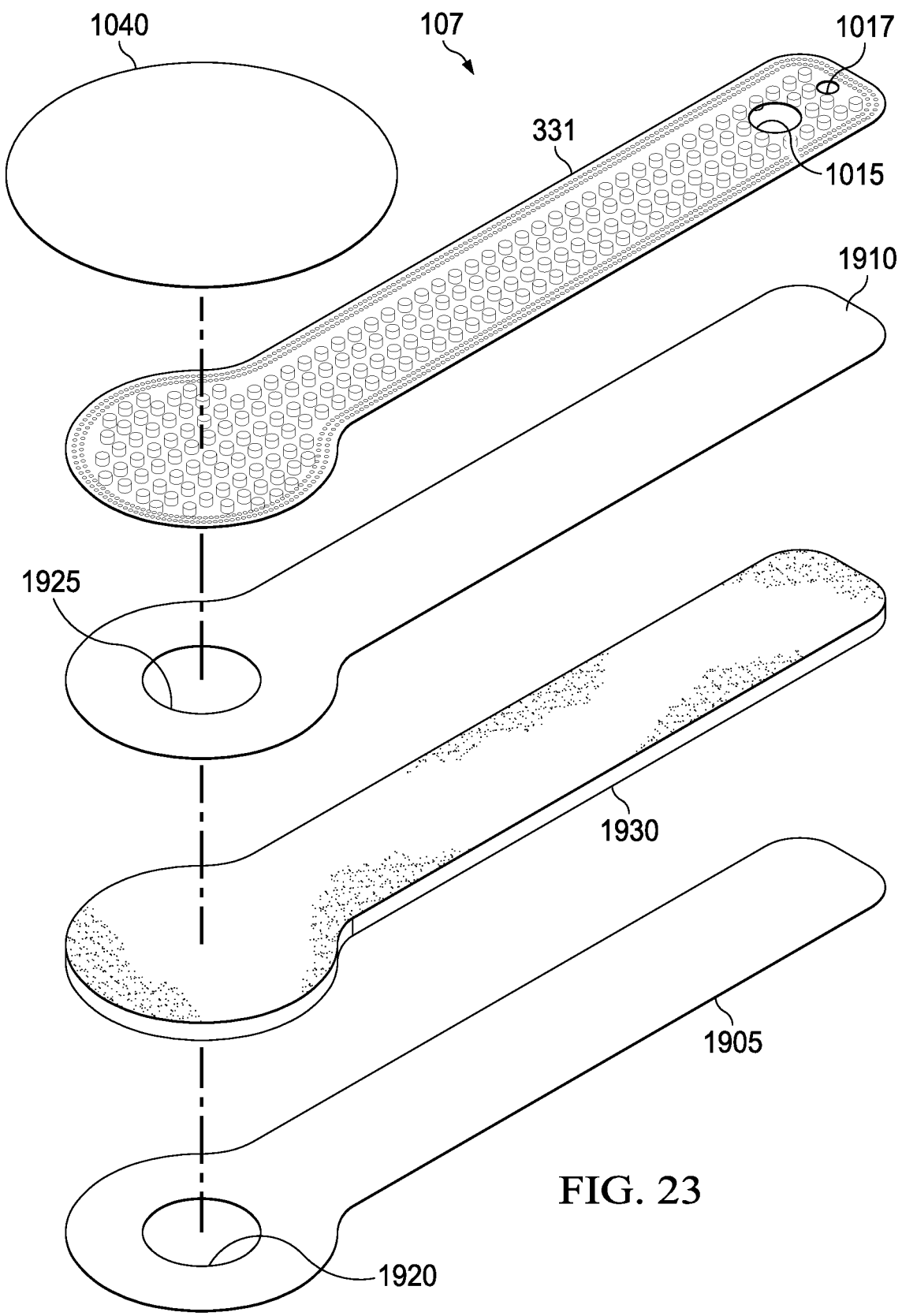
FIG. 23 is an assembly view of another example of a dressing interface, illustrating additional details that may be associated with some embodiments.
Figure 24:
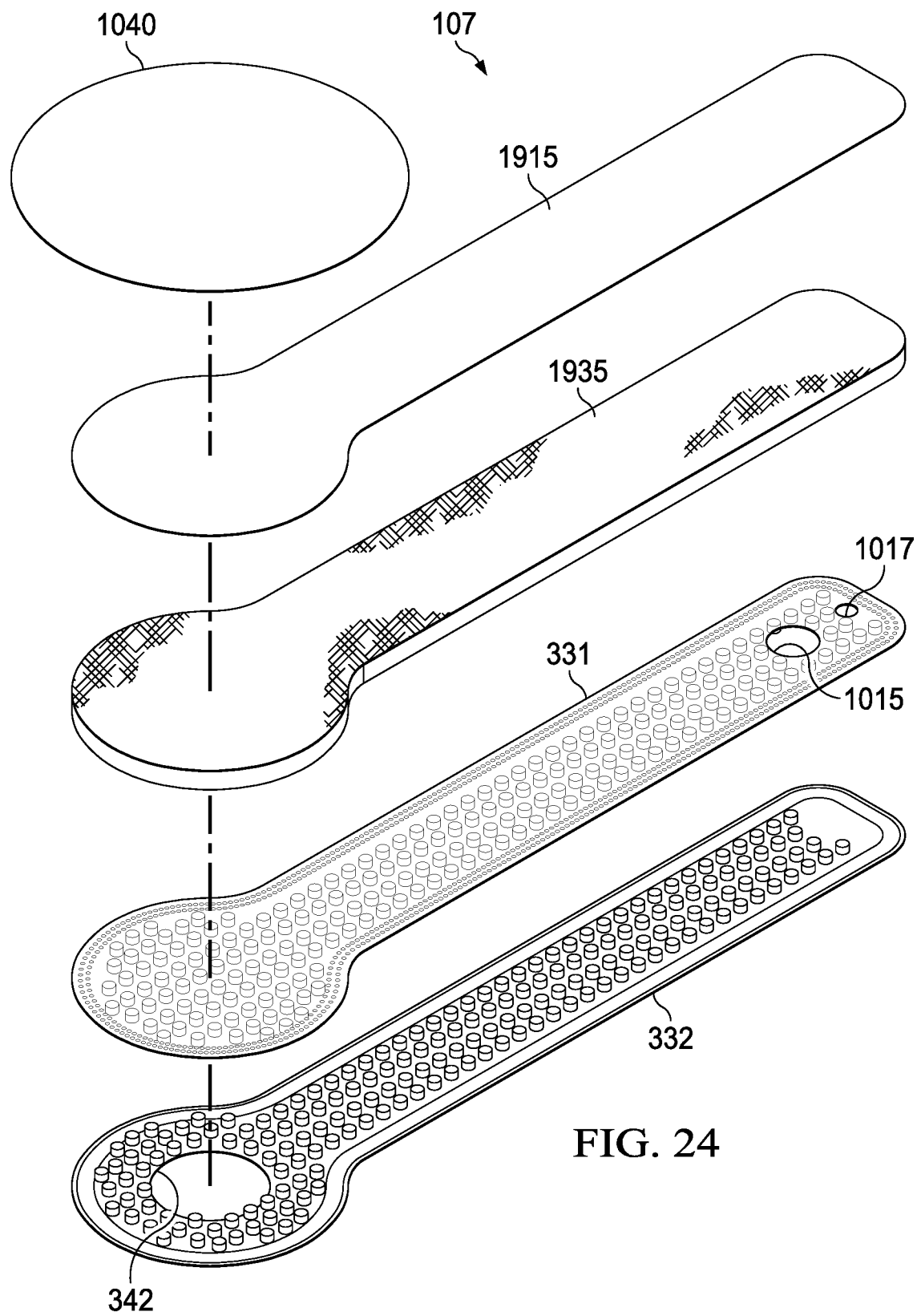
FIG. 24 is an assembly view of another example of a dressing interface, illustrating additional details that may be associated with some embodiments.

In some embodiments, one or more of the first layer 1905, the second layer 1910, and the third layer 1915 may additionally or alternatively comprise or consist essentially of a layer substantially similar to the first layer 331, the second layer 332, or both. In some examples, one or more of the first manifold 1930 and the second manifold 1935 may be omitted if one or more of the first layer 1905, the second layer 1910, and the third layer 1915 are replaced with the first layer 331 or the second layer 332. FIG. 23, for example, illustrates an embodiment of the dressing interface 107 in which the third layer 1915 is replaced by the first layer 331 and the second manifold 1935 is omitted. FIG. 24 illustrates an example in which the first layer 1905, the second layer 1910, and the first manifold 1930 are replaced by the first layer 331 and the second layer 332.

Some embodiments of the therapy system 100 may overcome problems associated with having a large head pressure in a closed pneumatic environment and the problems associated with using a vent disposed on or adjacent the dressing. For example, some embodiments of the therapy system 100 may resolve such problems by fluidly coupling the therapeutic environment to a fluid regulator such as, for example, the regulator 118 in FIG. 1, through any one of the fluid pathways so that the fluid regulator is separated from the dressing 102. For example, either one of the pressure-sensing pathways 334 or 338 may be used as a fluid conductor between the therapeutic space and the regulator 118. In some embodiments, the regulator 118 can maintain a substantially constant airflow and provide a continuous flow of a mixture of wound fluids and ambient air into the canister. Moreover, such embodiments can reduce the head pressure associated with the fluid conductors so that a negative-pressure source can achieve the same target pressure with a lower supply pressure. Such therapy systems utilizing a regulator such as the regulator 118 can increase safety and reduce power requirements for generating the same target pressure. Such therapeutic systems including airflow regulators can also facilitate detection of blockages in the fluid conductors because erroneous blockages may be less likely to be confused with the elimination of a systemic leak.

In some embodiments, the regulator 118 can provide a controlled airflow as opposed to a constant airflow. The controller 110 may be programmed to periodically open the regulator 118, which can allow ambient air to flow into the fluid pathway and the dressing interface 107 for a predetermined duration of time and, consequently, provide a predetermined volume of airflow into the pneumatic system. This feature can allow the controller 110 to purge blockages that may develop in the fluid pathways or the recessed space during operation. In some embodiments, the controller 110 may be programmed to open the regulator 118 for a fixed period of time at predetermined intervals such as, for example, for five seconds every four minutes to mitigate the formation of any blockages.

In some embodiments, the controller 110 may be programmed to open the regulator 118 in response to a stimulus within the pneumatic system rather than, or in addition to, being programmed to function on a predetermined therapy schedule. For example, if a pressure sensor is not detecting pressure decay in the canister, this may be indicative of a column of fluid forming in the fluid pathway or the presence of a blockage in the fluid pathway. Likewise, the controller 110 may be programmed to recognize that an expected drop in canister pressure as a result of opening the regulator 118 may be an indication that the fluid pathway is open. The controller 110 may be programmed to conduct such tests automatically and routinely during therapy so that the patient or caregiver can be forewarned of an impending blockage. The controller 110 may also be programmed to detect a relation between the extent of the deviation in canister pressure resulting from the opening of the regulator 118 and the volume of fluid with in the fluid pathway. For example, if the pressure change within the container 112 is significant when measured, this could be an indication that there is a significant volume of fluid within the fluid pathway. However, if the pressure change within the container 112 is not significant, this could be an indication that the plenum volume was larger.

The systems, apparatuses, and methods described herein may provide other significant advantages. For example, when the first and second fluid conductors are combined into a single fluid conductor as described above, the single fluid conductor may simplify use of the system. Additionally, the single fluid conductor may be fluidly coupled directly to the canister, allowing the user or caregiver to connect only one conductor to the therapy system rather than two separate fluid conductors.

Another advantage is that disposable elements can be combined with the mechanical elements in a variety of different ways to provide therapy. For example, in some embodiments, the disposable and mechanical systems can be combined inline, externally mounted, or internally mounted. Additionally, the applicator and the bridge of the dressing interfaces described above may be formed as separate components that are coupled together to form a single device. In yet other embodiments, the applicator and the bridge may be separate components that may be used independently of each other as a single component in the therapy system.

While shown in a few illustrative embodiments, a person having ordinary skill in the art will recognize that the systems, apparatuses, and methods described herein are susceptible to various changes and modifications. For example, certain features, elements, or aspects described in the context of one example embodiment may be omitted, substituted, or combined with features, elements, and aspects of other example embodiments. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for managing fluid in a system for treating a tissue site, the apparatus comprising:
    a first polymeric film having an outer surface, and an inner surface, the first polymeric film forming a plurality of features extending from the inner surface, the first polymeric film being non-porous;
    a second polymeric film having an outer, tissue-facing surface and an inner surface, the second polymeric film coupled to the first polymeric film and covering the plurality of features to form an enclosed space between the inner surface of the first polymeric film and the inner surface of the second polymeric film and a plurality of flow channels within the enclosed space, the second polymeric film having an aperture open to the enclosed space and adapted to fluidly couple the enclosed space to the tissue site;
    a first wall coupled between the inner surface of the first polymeric film and the inner surface of the second polymeric film, the first wall extending a length of the enclosed space from the aperture to an opposite end, the first wall forming a first fluid pathway and a second fluid pathway within the enclosed space in fluid communication through the aperture; and
    a port fluidly coupled to the first fluid pathway and the second fluid pathway.

2. The apparatus of claim 1, wherein the plurality of features is a plurality of blisters having a closed end.

3. The apparatus of claim 2, wherein the plurality of blisters extend into the enclosed space.

4. The apparatus of claim 2, wherein the blisters have a circular base having an average diameter between about 1 mm and about 10 mm.

5. The apparatus of claim 2, wherein the blisters have an average height between about 2 mm and about 5 mm.

6. The apparatus of claim 2, wherein the blisters have an average pitch between about 1 mm and about 10 mm between adjacent closed cells.

7. The apparatus of claim 2, wherein the first polymeric film and the second polymeric film is polyurethane having a yield strength greater than about 10 MPa.

8. The apparatus of claim 2, wherein the first polymeric film and the second polymeric film is polyurethane having an average thickness of about 500 µm and wherein the blisters have a draw ratio ranging from about 4:1 to about 10:1.

9. The apparatus of claim 2, wherein the first polymeric film and the second polymeric film is polyurethane having an average thickness of about 400 µm and wherein the blisters have a draw ratio ranging from about 5:1 to about 13:1.

10. The apparatus of claim 2, wherein the first polymeric film and the second polymeric film is polyurethane having an average thickness of about 600 µm and wherein the blisters have a draw ratio ranging from about 3:1 to about 9:1.

11. The apparatus of claim 1, wherein the first polymeric film and the second polymeric film are transparent.

12. The apparatus of claim 1, wherein the first polymeric film and the second polymeric film are translucent.

13. The apparatus of claim 1, wherein the second polymeric film includes a plurality of features extending into the enclosed space.

14. The apparatus of claim 1, wherein the port comprises a first port coupled to the first fluid pathway and adapted to be fluidly coupled to a source of negative pressure.

15. The apparatus of claim 14, wherein the port further comprises a second port coupled to the second fluid pathway and adapted to be fluidly coupled to a pressure sensor.

16. The apparatus of claim 14, wherein the port further comprises a second port coupled to the second fluid pathway and adapted to be fluidly coupled to a source of fluids.

17. The apparatus of claim 1, further comprising a second wall between the inner surface of the first polymeric film and the inner surface of the second polymeric film to form a third fluid pathway within the enclosed space in fluid communication with the aperture.

18. The apparatus of claim 17, wherein the port comprises a first port coupled to the first fluid pathway and adapted to be fluidly coupled to a source of negative pressure.

19. The apparatus of claim 18, wherein the port further comprises a second port coupled to the second fluid pathway and a third port coupled to the third fluid pathway, wherein both the second port and the third port are adapted to be fluidly coupled to a pressure sensor.

20. The apparatus of claim 1, wherein the first polymeric film and the second polymeric film are elongated shapes having the aperture formed at a distal end of the apparatus and the port formed at a proximal end of the apparatus.

21. The apparatus of claim 20, wherein the first polymeric film and the second polymeric film comprise a bridge portion between the distal end and the proximal end wherein the distal end is wider than the bridge portion.

22. The apparatus of claim 1, wherein there is no foam in the enclosed space.

23. The apparatus of claim 1, wherein there is no absorbent in the enclosed space.

* * * * *